United States Patent
Aizu et al.

(10) Patent No.: US 8,180,060 B2
(45) Date of Patent: May 15, 2012

(54) TELEMEDICAL SYSTEM

(75) Inventors: Kazuhiro Aizu, Osaka (JP); Yosuke Tajika, Hyogo (JP); Daisuke Kobayashi, Osaka (JP); Hiromichi Nishiyama, Osaka (JP); Masao Nonaka, Osaka (JP); Natsume Matsuzaki, Osaka (JP); Kaoru Yokota, Hyogo (JP); Yuichi Futa, Osaka (JP)

(73) Assignee: Panasonic Corporation, Osaka (JP)

( * ) Notice: Subject to any disclaimer, the term of this patent is extended or adjusted under 35 U.S.C. 154(b) by 938 days.

(21) Appl. No.: 12/194,740

(22) Filed: Aug. 20, 2008

(65) Prior Publication Data

US 2009/0103735 A1    Apr. 23, 2009

(30) Foreign Application Priority Data

Oct. 19, 2007    (JP) .................. 2007-272115

(51) Int. Cl.
*H04L 9/00* (2006.01)
*H04L 9/08* (2006.01)
*H04L 29/06* (2006.01)
*H04L 9/32* (2006.01)

(52) U.S. Cl. ........ 380/277; 380/278; 380/279; 380/280; 380/281; 380/282; 380/283; 380/284; 380/285; 713/150; 713/155; 713/167; 713/168; 600/300

(58) Field of Classification Search .......... 380/277–385; 600/300; 713/150, 155, 167, 168
See application file for complete search history.

(56) References Cited

U.S. PATENT DOCUMENTS

| 6,449,651 | B1 * | 9/2002 | Dorfman et al. ............. 709/229 |
| 6,708,272 | B1 * | 3/2004 | McCown et al. ............ 713/151 |
| 7,270,633 | B1 |  9/2007 | Goscha et al. |
| 7,694,132 | B2 * | 4/2010 | Ogram ......................... 713/162 |
| 2001/0031997 | A1 | 10/2001 | Lee |

(Continued)

FOREIGN PATENT DOCUMENTS

JP    2003-76791    3/2003

(Continued)

OTHER PUBLICATIONS

Extended European Search Report (in English language) mailed on Sep. 7, 2011 in corresponding European Patent Application No. 08162204.5.

(Continued)

*Primary Examiner* — Carl Colin
*Assistant Examiner* — Catherine Thiaw
(74) *Attorney, Agent, or Firm* — Wenderoth, Lind & Ponack, L.L.P.

(57) ABSTRACT

In the telemedical system securely sharing encryption keys for enabling secure exchange of the encrypted biological data between the measurement terminal and the server to prevent the data from being stolen by the malicious third party, a service key is transferred to the second adapter attached to a measurement terminal from the server via the first adapter attached to the management apparatus. First, the first adapter attached to the management apparatus receives the service key from the server. Next, the first adapter is temporarily detached from the management apparatus and is attached to the measurement terminal to store the symmetric key. The first adapter is detached from the measurement terminal, and is attached to the management apparatus again. The service key received in the first adapter is encrypted using the symmetric key, and the encrypted key is transmitted to the second adapter attached to the measurement terminal.

13 Claims, 13 Drawing Sheets

U.S. PATENT DOCUMENTS

| | | |
|---|---|---|
| 2004/0005061 A1* | 1/2004 | Buer et al. .................... 380/282 |
| 2004/0010688 A1* | 1/2004 | Matsuzaki et al. ............ 713/169 |
| 2004/0034776 A1* | 2/2004 | Fernando et al. ............. 713/171 |
| 2004/0194108 A1* | 9/2004 | Masui et al. .................. 718/105 |
| 2004/0260363 A1 | 12/2004 | Arx et al. |
| 2006/0218397 A1* | 9/2006 | Brown et al. ................. 713/168 |
| 2006/0253700 A1* | 11/2006 | Della-Libera et al. ........ 713/151 |
| 2007/0083759 A1* | 4/2007 | Drew et al. ................... 713/168 |
| 2007/0089163 A1* | 4/2007 | Denton ............................. 726/2 |
| 2007/0197878 A1* | 8/2007 | Shklarski ...................... 600/300 |
| 2007/0208233 A1* | 9/2007 | Kovacs ......................... 600/300 |
| 2008/0016348 A1* | 1/2008 | Craft et al. .................... 713/168 |
| 2008/0021834 A1* | 1/2008 | Holla et al. ..................... 705/51 |
| 2008/0114978 A1* | 5/2008 | Lehtovirta et al. ............ 713/155 |
| 2008/0148047 A1* | 6/2008 | Appenzeller et al. ......... 713/162 |
| 2008/0178009 A1* | 7/2008 | Funahashi ..................... 713/186 |
| 2008/0235508 A1* | 9/2008 | Ran et al. ...................... 713/151 |
| 2008/0247540 A1* | 10/2008 | Ahn et al. ........................ 380/44 |
| 2008/0273697 A1* | 11/2008 | Greco et al. ..................... 380/44 |
| 2009/0046860 A1* | 2/2009 | Bichler et al. ................. 380/270 |
| 2009/0061912 A1* | 3/2009 | Brown et al. .................. 455/466 |
| 2009/0067633 A1* | 3/2009 | Dawson et al. ............... 380/279 |
| 2009/0103734 A1* | 4/2009 | Hammell et al. .............. 380/278 |
| 2009/0208019 A1* | 8/2009 | Celik et al. .................... 380/277 |
| 2009/0234672 A1* | 9/2009 | Dicks et al. ........................ 705/3 |
| 2009/0264712 A1* | 10/2009 | Baldus et al. ................. 600/300 |
| 2010/0150347 A1* | 6/2010 | Teruyama ..................... 380/255 |

FOREIGN PATENT DOCUMENTS

JP 2006-228174 8/2006

OTHER PUBLICATIONS

Chapter 12: Key Establishment Protocols Ed—Menezes A J; Van Oorschot P C; Vanstone S A:, Handbook of Applied Cryptography; CRC Press Series on Discrete Mathematics and its Applications, Boca Raton, FL, US, pp. 489-541, Oct. 1, 1996, XP001525012, ISBN: 978-0-8493-8523-0.

* cited by examiner

TELEMEDICAL SYSTEM

BACKGROUND OF THE INVENTION (1) Field of the Invention

The present invention relates to telemedical systems, and particularly to a telemedical system in which keys for encrypting biological data are shared securely.

(2) Description of the Related Art

In recent years, awareness about health has been growing. One example that demonstrates the trend is measures against obesity, and with the coming of aging society, demand for comprehensive medical services has been rising.

However, some are unable to receive sufficient medical attention due to the distance to a medical facility that poses a barrier for visiting the facility for medical examination. In addition, from the perspective of preventative medical care, there is a growing demand for detailed services which enables a user to measure or refer to his/her health condition anytime and anywhere to improve the user's health condition.

Various technical solutions have been proposed to solve the problems and to meet the demand. For example, sensors for measuring biological data such as body weight and blood pressure have been miniaturized and improved in accuracy, which enables sensing of more biological data. Meanwhile, the network technology has rapidly advanced along with the spread of the broadband network such as optical fiber networks, the increase in the number of hotspot access points, and the development of WiMAX. In response to the advancement, it is expected that a combination of the sensor technology and the network technology provides more advanced and convenient medical services. Prospective telemedical services using various telemedical systems include at-home medical examinations by doctor, provisions of a variety of supplemental information upon medical examination through constant monitoring of body weight and blood pressure, and health management by a user by referring to the user's body weight and blood pressure through a computer at home and a mobile phone when the user is out.

However, biological data such as body weight, body temperature and blood pressure is among the most important personal information. Thus, for implementing the above-described telemedical service that utilizes the network technology, it is necessary to prevent the biological data from being stolen, and to allow only the users to refer to the biological data by using techniques such as encryption.

In order to solve the problem, a health management support system that manages biological data by obtaining the biological data through a sensor and transmitting the data to a management server (for example, see Japanese Unexamined Patent Application Publication No. 2003-76791).

In addition, a contents information providing system that provides diverse information including medical information based on information read from tags attached to goods, although the information being read is not limited to biological data (for example, see Japanese Unexamined Patent Application Publication No. 2006-228174).

However, in the configuration shown in Japanese Unexamined Patent Application Publication No. 2003-76791, communication between the biological sensor and the dedicated terminal and between the dedicated terminal and the management center is encrypted, but not between the biological sensor and the management center. Due to this configuration, there is a possibility that the biological data is exposed in the dedicated terminal. In addition, since the key is embedded in the sensor, the key may also leak when the sensor is analyzed.

Furthermore, in the configuration shown in Japanese Unexamined Patent Application Publication No. 2006-228174, although encrypted communication is performed between the IC tag and the server, there is no description or suggestion for a key management method. Thus, the key may leak when the IC tag is analyzed.

As described above, with the conventional techniques, there is a possibility that an encryption key for encrypting biological data exchanged between a measurement terminal and a server leaks, which makes it difficult to prevent the data from being stolen by a malicious third party.

In view of the above-described problems, it is an object of the present invention to provide a telemedical system that can prevent the biological data from being stolen by a malicious third party by securely sharing symmetric keys for encrypting the biological data exchanged between the measurement terminal and the server.

SUMMARY OF THE INVENTION

In order to solve the above-described problem, a telemedical system according to one aspect of the present invention includes a management apparatus, a measurement apparatus and, a server. A service key is transferred from the server to a second adapter attached to a measurement terminal via a first adapter attached to a management apparatus. The first adapter attached to the management apparatus receives the service key from the server. Next, the first adapter is temporarily detached from the management apparatus and is attached to the measurement terminal to store a symmetric key. The first adapter is detached from the measurement terminal, and is attached to the management apparatus again. The service key received in the first adapter is encrypted using the symmetric key, and the encrypted key is transmitted to the second adapter attached to the measurement terminal. The service key used for encryption can be shared in the telemedical system.

In the telemedical system according to the one aspect of the present invention, keys for encryption can be securely shared. This enables secure exchange of the encrypted biological data between the measurement terminal and the server, and therefore the present invention can prevent the data from being stolen by the malicious third party.

FURTHER INFORMATION ABOUT TECHNICAL BACKGROUND TO THIS APPLICATION

The disclosure of Japanese Patent Application No. 2007-272115 filed on Oct. 19, 2007 including specification, drawings and claims is incorporated herein by reference in its entirety.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings.

DESCRIPTION OF THE PREFERRED EMBODIMENT(S)

Figure 1:
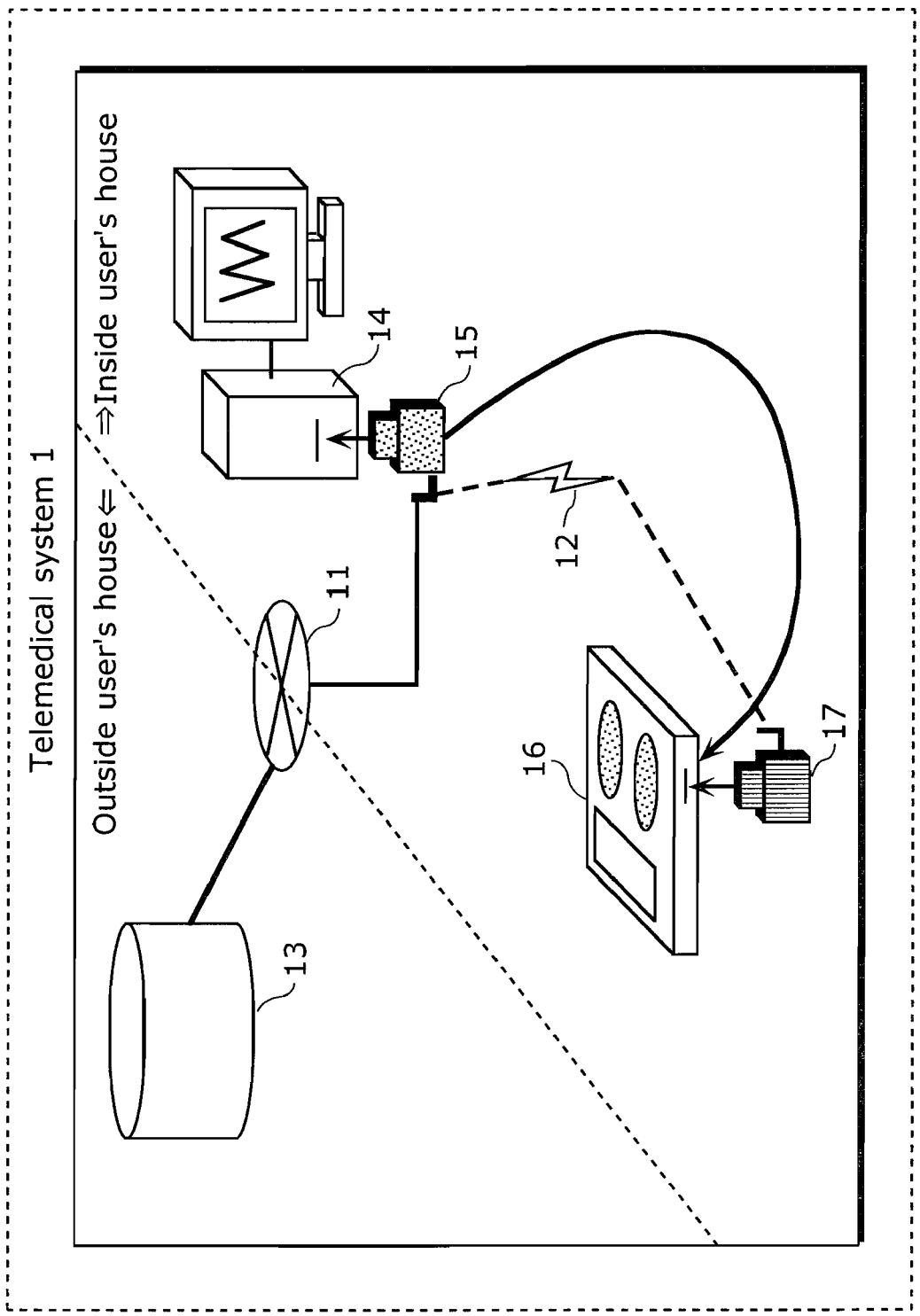
FIG. 1 shows an example of the telemedical system 1 according to the embodiment of the present invention.

The telemedical system in a first aspect of the present invention includes a first adapter that is attachable to a measurement terminal that obtains biological data of a user of the measurement terminal by measuring the user and to a management apparatus that manages the measured biological data; a second adapter that is attachable to the measurement terminal; and a server which communicates with the first adapter, in which the first adapter includes: a key holding unit which receives, from the server, a service key used for encrypting the biological data and to store the received service key, when the first adapter is attached to the measurement terminal; a first symmetric key generating unit which obtains unique information of the measurement terminal from the measurement terminal and to generate a symmetric key based on the obtained unique information, when the first adapter is attached to the management apparatus while the service key is stored in the key holding unit; a key encryption unit which encrypts the service key using the symmetric key and to store the encrypted service key in the key holding unit, when the first adapter is attached to the management apparatus; and a first communication unit which transmits the encrypted service key to the second adapter attached to the measurement terminal, and the second adapter includes: a second symmetric key generating unit which obtains from the measurement terminal the unique information of the measurement terminal and to generate a symmetric key based on the obtained unique information, when the second adapter is attached to the measurement terminal; a key decryption unit which decrypts the encrypted service key using the symmetric key generated in the second symmetric key generating unit, when the second adapter receives the encrypted service key from the first adapter; and a second communication unit which encrypts, using the decrypted service key, the biological data of the user measured by the measurement terminal and to transmit the encrypted biological data to the server via the first adapter.

According to this aspect, the service key is transferred to the second adapter attached to a measurement terminal from the server via the first adapter attached to the management apparatus. More specifically, first, the first adapter attached to the management apparatus receives the service key from the server. Next, the first adapter is temporarily detached from the management apparatus and is attached to the measurement terminal to store the symmetric key. The first adapter is detached from the measurement terminal, and is attached to the management apparatus again. The service key received in the first adapter is encrypted using the symmetric key, and the encrypted key is transmitted to the second adapter attached to the measurement terminal.

Accordingly, the symmetric key is obtained through hand-carry of the first adapter by the user, and thus the symmetric key does not leak outside the telemedical system via the network. Confidentiality of the service key is securely protected since the service key encrypted using the confidential symmetric key is transmitted to the measurement terminal and the service key is decrypted only in the measurement terminal. Furthermore, even when the measurement information from the measurement terminal is transmitted to the server, confidentiality of the transmitted measurement information is guaranteed since the measurement information is encrypted using the highly confidential service key.

In addition, the first adapter and the second adapter include control function such as decryption and encryption of the service key and generation of the symmetric key, and communication function. Thus, the management terminal or the measurement terminal may not necessarily include control function or communication function. This allows use of the conventional configuration to the measurement terminal, in addition to the reduction in the assembly cost of the measurement terminal.

Furthermore, in the telemedical system in the first aspect of the present invention, in the first adapter, the first symmetric key generating unit may not generate the symmetric key when the first adapter is attached to the measurement terminal while the service key is not stored in the key holding unit.

Furthermore, in the telemedical system in the first aspect of the present invention, the first symmetric key generating unit may delete the symmetric key and the service key after the first communication unit transmits the encrypted service key to the second adapter. Furthermore, in the telemedical system in the first aspect of the present invention, the second symmetric key generating unit may delete the symmetric key generated in the second symmetric key generating unit after the key decryption unit decrypts the encrypted service key using the symmetric key.

Furthermore, in the telemedical system in the first aspect of the present invention, the first symmetric key generating unit may generate the symmetric key based on the unique information of the measurement terminal using a predetermined calculation method, and the second symmetric key generating unit may generate the symmetric key based on the unique information of the measurement terminal using the predetermined calculation method.

Furthermore, in the telemedical system in the first aspect of the present invention, the first symmetric key generating unit and the second symmetric key generating unit may generate the symmetric key using a hash function as the predetermined calculation method.

Furthermore, in the telemedical system in the first aspect of the present invention, the first symmetric key generating unit and the second symmetric key generating unit may generate the symmetric key using a unique identifier of the measurement terminal as the unique information of the measurement terminal.

Furthermore, the telemedical system in a second aspect of the present invention includes a first adapter in a telemedical system including the first adapter, a second adapter, and a server, the first adapter being attachable to a measurement terminal that measures biological data of a user of the measurement terminal and being attachable to a management apparatus that manages the measured biological data, the second adapter being attachable to the measurement terminal, and the server communicating with the first adapter, the first adapter including: a key holding unit which receives a service key used for encrypting the biological data, from the server and to store the received service key when the first adapter is attached to the measurement terminal; a symmetric key generating unit which obtains unique information of the measurement terminal from the measurement terminal and to generate a symmetric key based on the obtained unique information, when the first adapter is attached to the management apparatus while the service key is stored in the key holding unit; a key encryption unit which encrypts the service key using the symmetric key and to store the encrypted service key in the key holding unit, when the first adapter is attached to the management apparatus; and a communication unit which transmits the encrypted service key to the second adapter attached to the measurement terminal.

The above-described aspects may not only be implemented as an apparatus, but also be implemented as an integrated circuit including processing units included in the apparatus, a method including the processing units configuring the apparatus as steps, or a program causing a computer to execute the steps. The program may be distributed via the recording medium such as CD-ROM, or the communication medium such as the Internet.

An embodiment of the telemedical system according to the present invention is hereafter described with reference to the drawings.

A telemedical system 1 is according to the embodiment of the present invention will be hereinafter described.

FIG. 1 shows an example of the telemedical system 1 according to the embodiment of the present invention. Here, as an example of specific service, a service in which a health care service vendor that operates the server 13 manages history of clients' (users') body weight data as their biological data using the network.

The telemedical system 1 includes the external network 11, the internal network 12, the server 13, the user terminal 14, the user terminal adapter 15, the measurement terminal 16, and the measurement terminal adapter 17.

Note that, although only one measurement terminal 16 and measurement terminal adapter 17 are illustrated in FIG. 1, there may be multiple measurement terminals 16 and multiple measurement terminal adapters 17. In addition, although the user terminal 14 includes a user interface, the user terminal 14 may operate as a gateway without a user interface function.

The server 13 and the user terminal 14 are connected to the external network 11. The external network 11 is a Wide Area Network such as the Internet. Note that the external network 11 may be a network, for example, a telephone line or a dedicated line.

The user terminal adapter 15 and the measurement terminal adapter 17 are connected to the internal network 12. The internal network 12 is a short range wireless communication path, and is implemented, for example, by Bluetooth™.

The server 13 provides the user terminal 14 with the body weight management service. For example, the server 13 provides the services including:

(1) distribution of a service key to the measurement terminal adapter 17 inserted in the measurement terminal 16 of a registered user via the user terminal adapter 15 inserted in the user terminal 14;

(2) collection of encrypted body weight data collected in the user terminal 14; and (3) data provision for display of the body weight data collected in the server 13 in the user terminal 14.

The user terminal 14 is operated by the user, and is, for example, a personal computer or a digital television. Furthermore, the user terminal 14 includes a slot to which the user terminal adapter 15 can be inserted.

When the user terminal adapter 15 is inserted, the user terminal 14 is capable of, for example, joining the body weight data management service provided by the vendor offering health care service and operating the server 13 and displays the body weight data. More specifically, the user terminal 14 to which the user terminal adapter 15 is inserted can provide the user with the following services:

(1) user registration at the server 13;

(2) collection of the body weight data measured in the measurement terminal 16;

(3) registration of the collected encrypted bodyweight data on the server 13; and (4) display of the history of the body weight data managed in the server 13.

Here, the measurement terminal 16 is a weighing scale that can measure the user's body weight. Furthermore, the measurement terminal 16 includes a slot to which the measurement terminal adapter 17 can be inserted. When the measurement terminal adapter 17 is inserted, the measurement terminal 16 is capable of registering the body weight data on the server 13 via the user terminal 14. More specifically, the measurement terminal 16 to which the measurement terminal adapter 17 is inserted, can provide the following services:

(1) measurement of the user's body weight; and (2) encryption of the measured body weight data using a service key and transmits the encrypted body weight data to the user terminal 14.

Note that the user terminal adapter 15 is inserted to the slot in the user terminal 14 when in use. The user terminal adapter 15 can provide the user with the following services:

(1) reception of the service key from the server 13 via the external network 11;

(2) transmission of the service key encrypted using a symmetric key generated from the unique information of the measurement terminal 16 to the measurement terminal adapter 17;

(3) transmission of the measured body weight data to the server 13 via the external network 11 after the body weight data is encrypted using the service key in the measurement terminal adapter 17; and (4) obtainment of the body weight data managed in the server 13 and display of the body weight data on the user terminal 14.

Here, instead of the user terminal 14, the user terminal adapter 15 receives and holds the service key transmitted from the server 13 in order to prevent the data from being stolen by a malicious third party or leaks of the data to a third party.

The measurement terminal adapter 17 is inserted to the slot in the measurement terminal 16 when in use.

The measurement terminal adapter 17 performs the following:

(1) reception of the service key from the user terminal adapter 15; and (2) encryption of the body weight data measured in the measurement terminal 16 and transmission of the body weight data to the user terminal adapter 15 via the internal network 12.

Here, instead of the measurement terminal 16, the measurement terminal adapter 17 holds the service key in order to prevent the data from being stolen by a malicious third party or leaks of the data to a third party. The measurement terminal adapter 17 encrypts and transmits the encrypted biological data such as body weight data for the same reason.

As described above, the user terminal 14 and the measurement terminal 16 do not hold the service key for encrypting the body weight which is biological data, in order to prevent the biological data from being stolen by the malicious third party and from leaking to a third party by lowering the possibility of the stealing and the leak. The user terminal adapter 15 and the measurement terminal adapter 17 hold the service key.

Note that the description of an aspect for secure sharing of the service key which is a key for encryption is to be described later, and thus the description is omitted here.

<Configuration of the Server 13>

Figure 2:
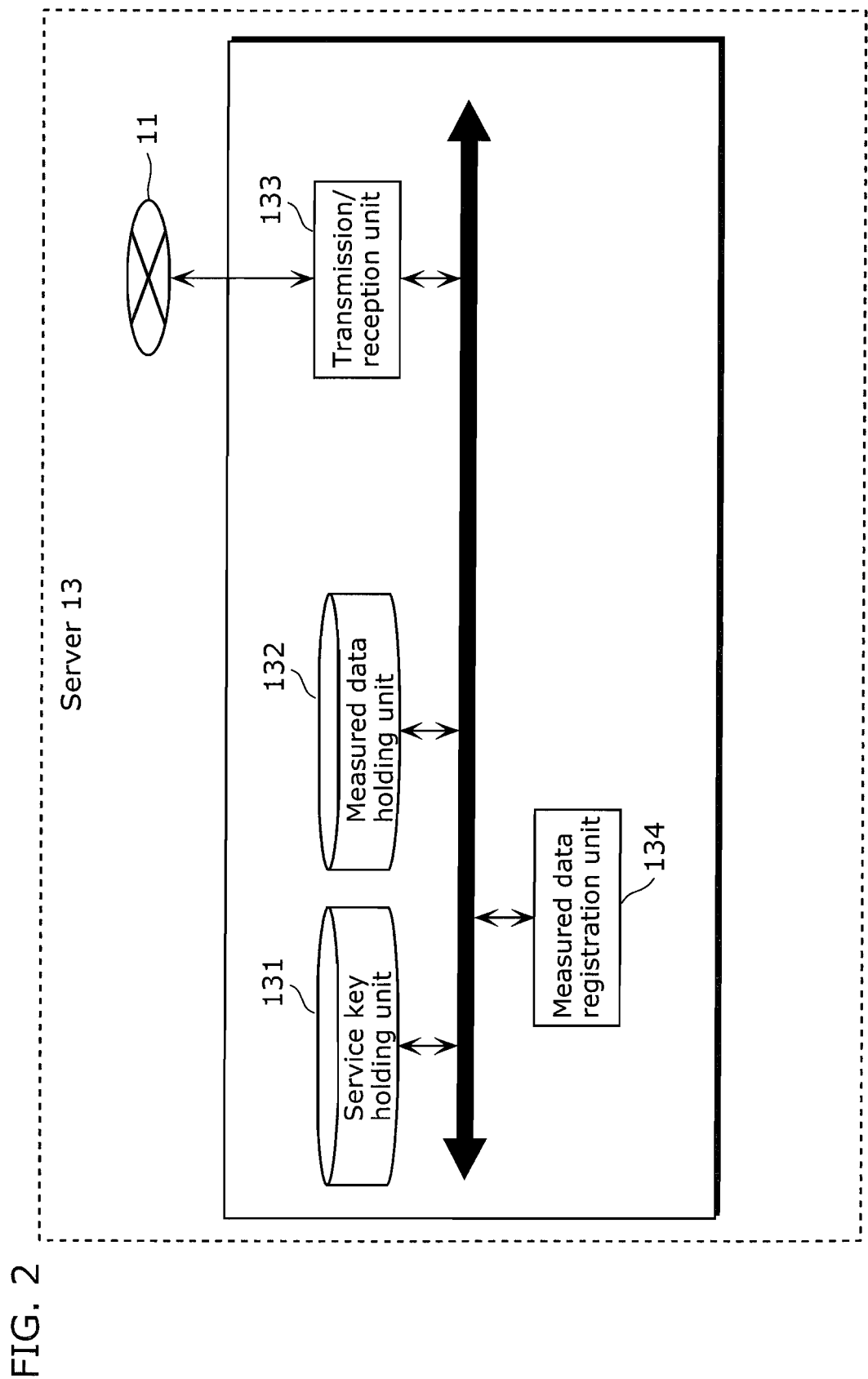
FIG. 2 shows the configuration of the server according the embodiment of the present invention.

FIG. 2 shows the configuration of the server according the embodiment of the present invention.

As shown in FIG. 2, the server 13 includes the service key holding unit 131, the measured data holding unit 132, the transmission/reception unit 133 and the measured data registration unit 134.

The service key holding unit 131 holds the service key. Here, the service key takes values of, for example, 128 bits, 192 bits, or 256 bits, and is generated using random numbers when the server 13 is activated and in operation.

The measured data holding unit 132 holds the user's measured data. More specifically, multiple sets of user identifiers, user information, and, for example, biological measurement data which is measurement of biological data such as the body weight data measured in the measurement terminal 16. The user identifier is, for example, a unique value of 128 bits, 192 bits, or 256 bits. The user information is information of the user such as name, gender, address, and telephone number. The biological measurement data is composed of a set of data including the date and time of measurement and the data measured in the measurement terminal 16. For example, when the biological measurement data is body weight data, the biological measurement data is denoted as "2007/9/1: 70.1, 2007/9/2: 70.3 . . . 2007/9/20: 69.9."

The transmission/reception unit 133 transmits/receives data (including message) to/from the user terminal adapter 15 inserted in the user terminal 14.

Furthermore, the transmission/reception unit 133 includes the function of outputting, when specific data is received, the specific data to a suitable component. For example, when measured data encrypted using the service key from the user terminal adapter 15 is received, the transmission/reception unit 133 outputs the received measured data to the measured data registration unit 134. When a message, from the measured data registration unit 134, notifying the completion of registering the received measured data is received, the transmission/reception unit 133 transmits the message to the user terminal adapter 15.

The measured data from the user terminal adapter 15 is inputted to the measured data registration unit 134 via the transmission/reception unit 133. The measured data registration unit 134 obtains user identifier and encrypted biological measurement data from the inputted measured data.

Furthermore, the measured data registration unit 134 obtains the service key from the service key holding unit 131. Then the measured data registration unit 134 decrypts the encrypted biological measurement data using the obtained service key, and obtains the biological measurement data. Here, the algorithm used for decryption is the same as the algorithm used for encrypting the biological measurement data in the user terminal adapter 15. More specifically, the decryption algorithm of the Advanced Encryption Standard (AES) is used.

<Operations of the Server 13>

The operations of the server 13 are described. Here, descriptions will be made for the following cases: (1) user registration; (2) measured data registration; and (3) display of measured data.

(1) User Registration

The transmission/reception unit 133 receives a message requesting user information registration including the user information from the user terminal adapter 15, and transmits the message requesting the received user information registration to the measured data registration unit 134.

The measured data registration unit 134 generates a new user identifier when receiving the message requesting user information registration. The measured data registration unit 134 associates the user information included in the message requesting user information registration and the generated user identifier, and stores the user information and the user identifier in the measured data holding unit 132.

The measured data registration unit 134 obtains the service key from the service key holding unit 131, and generates user information registration result data including the user identifier, the user information, and the service key. The measured data registration unit 134 outputs the generated user information registration result data to the transmission/reception unit 133.

The transmission/reception unit 133 transmits the received user information registration result data to the user terminal adapter 15, and terminates the operation.

As described above, the server 13 that provides the body weight data management service registers the user.

(2) Measured Data Registration

When the measured data from the user terminal adapter 15 is received, the transmission/reception unit 133 outputs the received measured data to the measured data registration unit 134.

When the measured data is inputted, the measured data registration unit 134 obtains user identifier and encrypted biological measurement data from the inputted measured data.

Next, the measured data registration unit 134 obtains the service key from the service key holding unit 131. Then the measured data registration unit 134 decrypts the encrypted biological measurement data using the obtained service key, and obtains the biological measurement data.

Next, the measured data registration unit 134 stores the user identifier and the decrypted biological measurement data in the measured data holding unit 132. After the data is stored, the measured data registration unit 134 transmits a message indicating the completion of registration of the biological measurement data to the user terminal adapter 15 and terminates the operation.

As described above, the server 13 that provides the body weight data management service registers the measured data of the user.

(3) Displaying of Measured Data

The transmission/reception unit 133 receives a message indicating request of transmission of the measured data including the user identifier. The transmission/reception unit 133 outputs the received message indicating the request for transmission of measurement data to the measured data registration unit 134.

The measured data registration unit 134 obtains user identifier from the inputted message indicating request of transmission of the measured data, and obtains the biological measurement data corresponding to the user identifier from the measured data holding unit 132.

Next, the measured data registration unit 134 generates measured data transmission data including the user identifier and the biological measurement data, transmits the generated measured data transmission data to the user terminal adapter 15, and terminates the operation.

As described above, the measured data of the user is obtained from the server 13 that provides the body weight data management service and the measured data is displayed.

Next, the configuration and operations of the user terminal 14 is hereafter described.

<Configuration of User Terminal 14>

Figure 3:
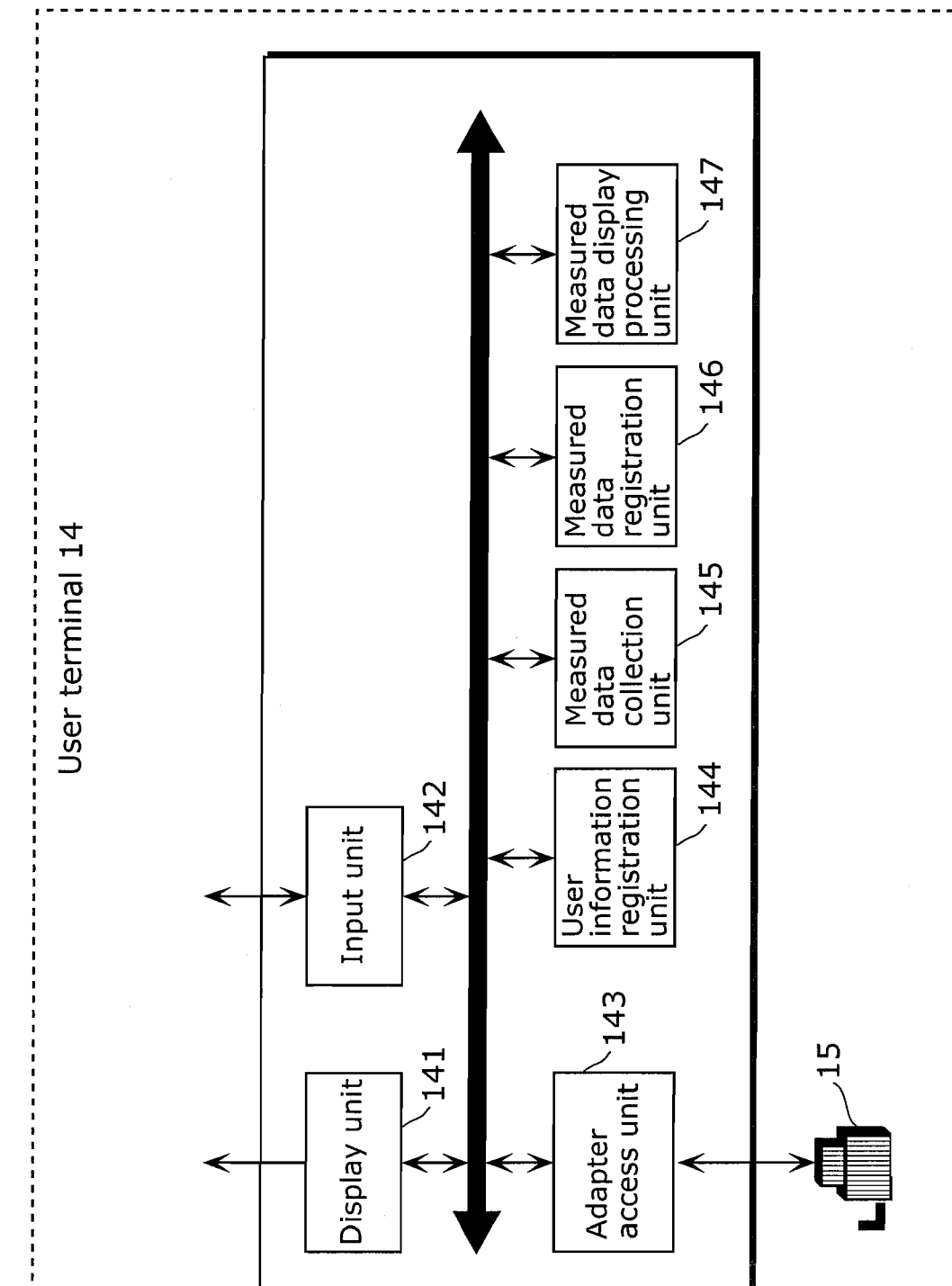
FIG. 3 shows the configuration of the user terminal according to the embodiment of the present invention.

FIG. 3 shows the configuration of the user terminal according to the embodiment of the present invention.

As shown in FIG. 3, the user terminal 14 includes the display unit 141, the input unit 142, the adapter access unit 143, the user information registration unit 144, the measured data collection unit 145, the measured data registration unit 146, and the measured data display processing unit 147. However, when the user does not require input/output, the display unit 141 and the input unit 142 may not be loaded.

The display unit 141 includes a display, and is capable of displaying a screen according to requests from other components of the user terminal 14.

The input unit 142 includes a keyboard or a mouse, and receives external input (by the user). When an external request for service activation is received, the input unit 142 accesses the adapter access unit 143 and confirms whether the user terminal adapter 15 is attached or not. When the user terminal adapter 15 is attached, the input unit 142 obtains the content of the service request from the user terminal adapter 15 via the adapter access unit 143, and displays a menu screen corresponding to the content of service request in the display unit 141. The input unit 142 outputs the content of the service request to the appropriate component according to the content of service request designated by the user, for example, the user registration.

The adapter access unit 143 exchanges data including messages and signals with the user terminal adapter 15. For example, when the user terminal adapter 15 is a USB, the adapter access unit 143 may be a USB slot or a USB terminal host. Furthermore, when the user terminal adapter 15 is an SDIO card, the adapter access unit 143 may be an SDIO slot or an SDIO terminal host.

The user information registration unit 144 waits until the signal indicating request of user registration from the input unit 142 is received. When a signal indicating request for user registration is received, the user information registration unit 144 transmits a message requesting registration of user information including the user information to the user terminal adapter 15 via the adapter access unit 143. In addition, the user information registration unit 144 receives, from the user terminal adapter 15 and via the adapter access unit 143, the signals indicating the completion of the user information registration at the server 13. Here, the signal indicating the completion of the user information registration includes user identifier and user information.

In addition, the user information registration unit 144 instructs the user terminal adapter 15 via the adapter access unit 143 to transmit the service key from the user terminal adapter 15 to the measurement terminal adapter 17. Here, the user terminal adapter 15 transmits the service key using a symmetric key generated from the unique information of the measurement terminal 16 obtained using a safe method without being stolen from the malicious third party. Note that the description is omitted here since the detail is described in detail later.

In addition, the user information registration unit 144 receives a service key distribution completion signal indicating the completion of transmission of the encrypted service key from the user terminal adapter 15 to the measurement terminal adapter 17.

The measured data collection unit 145 waits until a signal indicating collection of measured data from the input unit 142 is received. When the signal indicating collection of measured data is received, the measured data collection unit 145 transmits a measured data collection request message, to the measurement terminal adapter 17 via the adapter access unit 143 and the user terminal adapter 15, indicating that the biological measurement data, that is, the user's biological data measured in the measurement terminal 16 is collected.

The measured data collection unit 145 receives a measured data collection completion message indicating completion of reception of the biological measurement data collected in the measurement terminal adapter 17 from the user terminal adapter 15 via the adapter access unit 143.

The measured data registration unit 146 waits until a signal indicating instruction for registering measured data from the input unit 142 is received. When a signal indicating instruction for registering the measured data is received, the measured data registration unit 146 causes, via the adapter access unit 143, the user terminal adapter 15 to transmit the user information and the biological measurement data of the user encrypted using the service key to the server 13. Here, the measured data registration unit 146 causes the user terminal adapter 15 to receive the biological measurement data measured in the measurement terminal 16 and encrypted in the measurement terminal adapter 17 using the service key, and to transmit the encrypted biological measurement data to the server 13 via the external network 11.

The measured data registration unit 146 receives the message (or data) indicating the completion of registration of measured data in the server 13 from the user terminal adapter 15 via the adapter access unit 143.

The measured data display processing unit 147 waits until a signal indicating display of measured data of the user is received from the input unit 142. When the signal indicating display of measured data is received, the measured data display processing unit 147 transmits a message indicating request for transmission of measured data including the user identifier to the user terminal adapter 15 via the adapter access unit 143.

Figure 4:
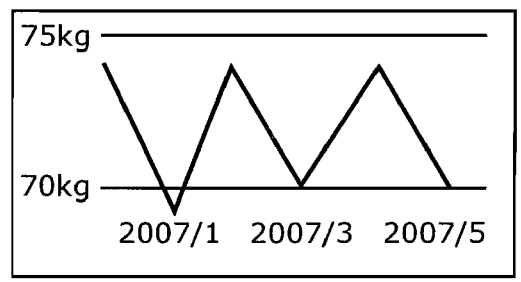
FIG. 4 shows an example screen displaying biological measurement data measured by a user.

Furthermore, the measured data display processing unit 147 receives measurement data transmission data that is decrypted in the encryption unit 1507 and includes the user identifier and the biological measurement data, and displays, for example, a measured data display screen as shown in FIG. 4 in the display unit 141.

Here, FIG. 4 is an example screen of biological measurement data measured by the user. FIG. 4 shows that the body-weight data shifts between approximately 70 kg and 75 kg from January 2007 to May 2007. With this, the user (displayed as Yamada Taro in FIG. 4), can check the history of body weight data, and help managing his health by, for example, exercising when his body weight is around 75 kg.

<Operations of User Terminal 14>

Next, the operations of the user terminal 14 are described. Here, descriptions will be made for the following cases: (1) user registration; (2) measured data collection; (3) measured data registration; and (4) display of measured data.

(1) User Registration

When the input unit 142 receives, from outside the user terminal 14 (for example, from the user), an activation request indicating that the user registration is performed, the input unit 142 accesses the adapter access unit 143, and checks whether the user terminal adapter 15 is attached. When the user terminal adapter 15 is not attached, the input unit 142 waits until the user terminal adapter 15 is attached and a service activation request is received from outside the user terminal 14 again.

Next, the input unit 142 transmits a signal indicating a user registration request to the user information registration unit 144.

When a signal indicating request for user registration is received, the user information registration unit 144 transmits a message requesting registration of user information including the user information to the user terminal adapter 15 via the adapter access unit 143.

In addition, the user information registration unit 144 receives, from the user terminal adapter 15 via the adapter access unit 143, the signals indicating the completion of the user information registration at the server 13, including the user identifier and the user information.

The user information registration unit 144 displays a screen indicating completion of user registration in response to the received signal indicating the completion of the user information registration in the display unit 141.

Note that, the user information may be inputted by the user when the input unit 142 transmits the signal indicating the request for user registration. The user information may also be inputted before the user information registration unit 144 transmits the message for requesting user information registration including the user information. Alternatively, although the number of steps in the procedure increases, the user information may be inputted and transmitted to the server 13 after the user information registration unit 144 transmits the message requesting the user information registration to the server 13 and before the server 13 needs the user information.

As described in the example above, the user is registered at the server 13 that is operated by the health care service vendor and provides a body weight data management service.

(2) Measured Data Collection

When the input unit 142 externally receives an activation request indicating that the measured data is to be collected externally, the input unit 142 accesses the adapter access unit 143, and checks whether the user terminal adapter 15 is attached or not. When the user adapter 15 is not attached, the input unit 142 terminates the operation.

Next, the input unit 142 transmits a signal indicating that the measured data is collected to the measured data collection unit 145.

When the signal indicating collection of measured data is received, the measured data collection unit 145 transmits a measured data collection request message, to the measurement terminal adapter 17 via the adapter access unit 143 and the user terminal adapter 15, indicating that the biological measurement data, that is, the user's biological data measured in the measurement terminal 16 is collected.

Next, the measured data collection unit 145 receives a measured data collection completion message indicating completion of reception of the measured data collected in the measurement terminal adapter 17 from the user terminal adapter 15 via the adapter access unit 143.

The measured data collection unit 145 causes the display unit 141 to display a screen indicating completion of collection of measured data based on the received message indicating completion of collection of measured data.

As described above, the collection of the measured data, that is, the body weight measured by the user is performed.

(3) Measured Data Registration

When the input unit 142 receives, from outside the user terminal 14, a service activation request indicating that the measured data is to be registered, the input unit 142 accesses the adapter access unit 143, and checks whether the user terminal adapter 15 is attached or not. When the user adapter 15 is not attached, the input unit 142 terminates the operation.

The input unit 142 then transmits signals indicating that the biological measurement data is registered to the measured data registration unit 146.

When the signal indicating that the measured data is to be registered is received, the measured data registration unit 146 transmits, via the adapter access unit 143, a measured data registration request message indicating that the measured data held in the user terminal adapter 15 is registered at the server. Subsequently, the measured data registration unit 146 causes the user terminal adapter 15 to transmit the user's biological measurement data that includes the user information and is encrypted using the service key to the server 13.

Then the measured data registration unit 146 receives a message indicating the completion of registering the measurement at the server 13 from the user terminal adapter 15 via the adapter access unit 143.

After that, the measured data registration unit 146 causes the display unit 141 to display a screen indicating the completion of registration of measured data based on the received message indicating the completion of registration of measured data.

As described in the example above, the measured data is registered at the server 13 operated by the vender that offers health care service and provides the body weight management service.

(4) Display of Measured Data

When the input unit 142 receives, from outside the user terminal 14, an activation request indicating that the measured data is to be displayed, the input unit 142 accesses the adapter access unit 143, and checks whether the user terminal adapter 15 is attached or not. When the user terminal adapter 15 is not attached, the operation is terminated.

Next, the input unit 142 transmits a signal indicating that the measured data is to be displayed to the measured data display processing unit 147.

When the signal indicating display of measured data is received, the measured data display processing unit 147 transmits a message requesting transmission of measured data including the user identifier to the user terminal adapter 15 via the adapter access unit 143.

Then, the measured data display processing unit 147 receives, via the adapter access unit 143, the measured data transmission data including the user identifier and the biological measurement data decrypted in the encryption unit 1507, and displays the measured data display screen as shown in FIG. 4 in the display unit 141.

As described in the example above, the measured data of the user is obtained from the server 13 that provides the body weight data management service and the measured data is displayed.

Next, the configuration and operations of the user terminal adapter 15 are hereafter described.

<Configuration of the User Terminal Adapter 15>

Figure 5:
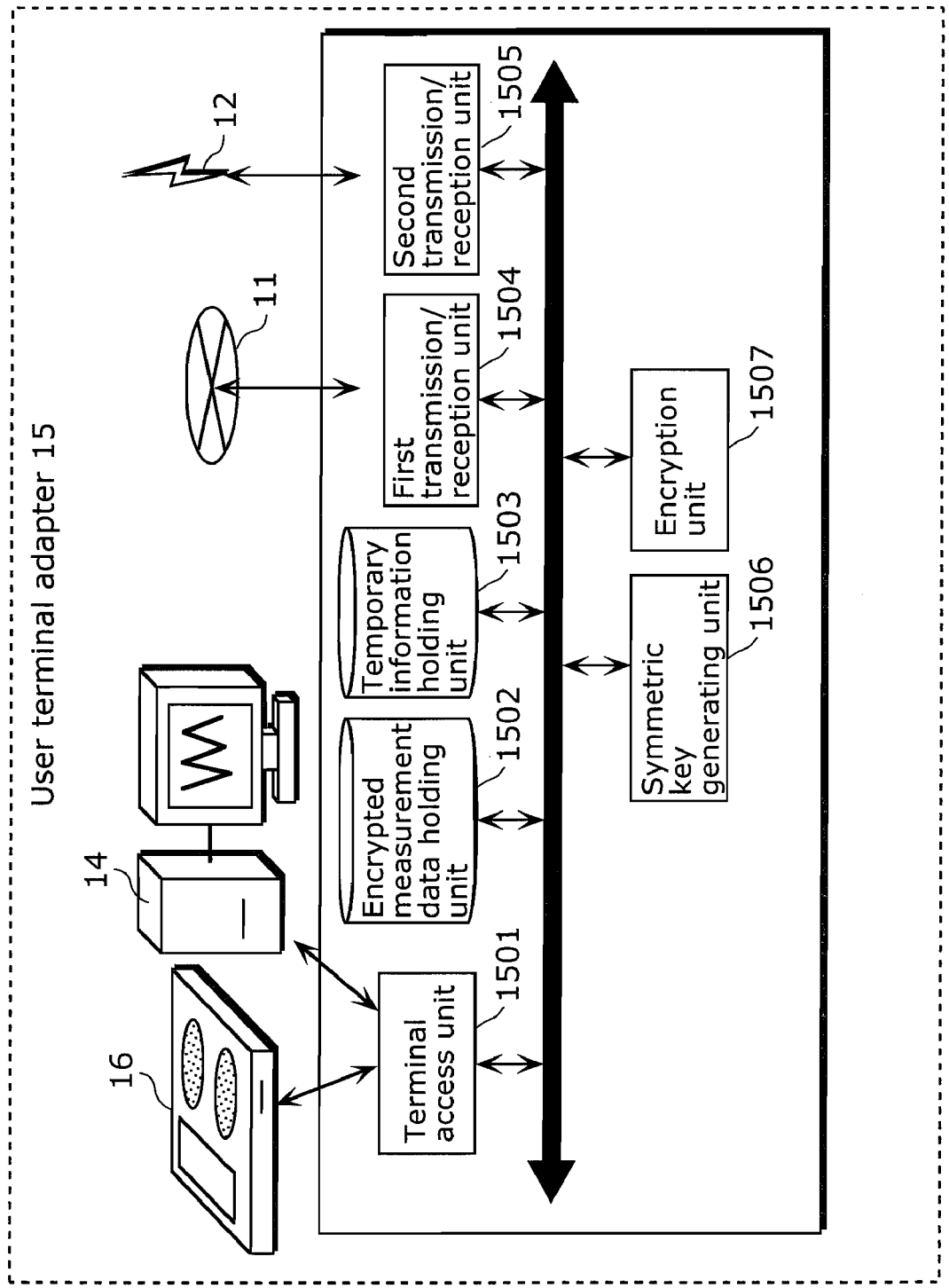
FIG. 5 shows the configuration of the user terminal adapter according to the embodiment of the present invention.

FIG. 5 shows the configuration of the user terminal adapter according to the embodiment of the present invention.

As shown in FIG. 5, the user terminal adapter 15 includes the terminal access unit 1501, the encrypted measurement data holding unit 1502, the temporary information holding unit 1503, the first transmission/reception unit 1504, the second transmission/reception unit 1505, the symmetric key generating unit 1506, and the encryption unit 1507.

The terminal access unit 1501 exchanges data with the user terminal 14 or the measurement terminal 16 to which the user terminal adapter 15 is inserted. For example, when the user terminal adapter 15 is a USB, the terminal access unit 1501 is a USB terminal or a host of USB device. Alternatively, when the user terminal adapter 15 is an SDIO card, the terminal access unit 1501 is an SDIO terminal or an SDIO card host.

The terminal access unit 1501 transmits attached device inquiry signal, and checks either the user terminal adapter 15 or the user terminal 14 to see if the user terminal adapter 15 is attached or not.

The terminal access unit 1501 checks, via the second transmission/reception unit 1505, if the user terminal adapter 15 can communicate with the measurement terminal adapter 17 attached to the measurement terminal 16 when it is confirmed that the user terminal adapter 15 is attached to the user terminal 14. The terminal access unit 1501 also checks whether the user terminal adapter 15 can communicate with the server 13 via the first transmission/reception unit 1504. The terminal access unit 1501 transmits, for example, the check result to the encryption unit 1507 that has sent an inquiry in response to the inquiry.

The encrypted measurement data holding unit 1502 holds encrypted measurement data.

The temporary information holding unit 1503 holds temporary data. More specifically, the temporary information holding unit 1503 holds the service key received from the server 13 and the symmetric key inputted from the symmetric key generating unit 1506.

The first transmission/reception unit 1504 transmits/receives data or message with the transmission/reception unit 133 in the server 13 via the external network 11.

When a specific data or message is received, the first transmission/reception unit 1504 can output the received specific data or message to a suitable component.

For example, when a message requesting registration of the user information from the user information registration unit 144 in the user terminal 14 is received, the first transmission/reception unit 1504 transmits the message to the server 13. When the user information registration result data is received, the first transmission/reception unit 1504 obtains a user identifier, user information, and a service key from the user information registration result data. The first transmission/reception unit 1504 stored the obtained user identifier and the user information in the encrypted measurement data holding unit 1502, and stores the obtained service key in the temporary information holding unit 1503.

In addition, when the user information registration result data is received from the server 13, the first transmission/reception unit 1504 outputs a signal indicating that the user information registration of the user identifier and the user information except the service key is completed to the user information registration unit 144 in the user terminal 14.

The second transmission/reception unit 1505 exchanges data with the second transmission/reception unit 173 in the measurement terminal adapter 17 via the internal network 12. Here, the internal network 12 that transmits/receives data is implemented by, for example, Bluetooth™.

The symmetric key generating unit 1506 generates a symmetric key from unique information such as the measurement terminal identifier of the measurement terminal 16.

The symmetric key generating unit 1506 obtains the measurement terminal identifier from the measurement terminal 16 via the terminal access unit 1501 when the user terminal adapter 15 is inserted to the slot in the measurement terminal 16 by hand-carry. The symmetric key generating unit 1506 then generates a symmetric key by performing computations based on the obtained measurement terminal identifier, and stores the generated symmetric key in the temporary information holding unit 1503.

Note that the computation method in the symmetric key generating unit 1506 for generating the symmetric key is same as the computation method used by the measurement terminal adapter 17 for generating a symmetric key from the unique information of the measurement terminal 16 (here, a measurement terminal identifier). The computation method uses, for example, the AES cryptographic algorithm or a one-way hash function algorithm such as the Message Digest Algorithm 5 (MD5).

The user terminal adapter 15 and the measurement terminal adapter 17 generate symmetric keys from the unique information of the same measurement terminal 16 using the same computation method; identical symmetric keys are generated although the user terminal adapter 15 and the measurement terminal adapter 17 generate symmetric keys independently.

The encryption unit 1507 checks the terminal access unit 1501 to see whether the user terminal adapter 15 is attached to the user terminal 14, and whether the user terminal adapter 15 can communicate with the measurement terminal adapter 17 attached to the measurement terminal 16.

When the user terminal adapter 15 is attached to the user terminal 14 and the user terminal adapter 15 can communicate with the measurement terminal adapter 17 attached to the measurement terminal 16, the encryption unit 1507 obtains the service key and the symmetric key stored in the temporary information holding unit 1503. The encryption unit 1507 encrypts the service key using the symmetric key. The encryption unit 1507 transmits the encrypted service key encrypted with the symmetric key to the measurement terminal adapter 17 attached to the measurement terminal 16. After the encrypted service key is transmitted to the measurement terminal adapter 17, the encryption unit 1507 outputs, to the user information registration unit 144 in the user terminal 14, a service key distribution completion signal indicating that the user terminal adapter 15 finished transmitting the encrypted service key to the measurement terminal adapter 17.

Note that, after the encrypted service key is transmitted, the encryption unit 1507 deletes the service key and the symmetric key stored in the temporary information holding unit 1503. This is suitable for minimizing a possibility that an encryption key for encrypting biological data exchanged between a measurement terminal and a server is stolen by a malicious third party or a leak of the biological data. The encryption unit 1507 may not have to delete the service key and the symmetric key stored in the temporary information holding unit 1503 after the encrypted service key is transmitted.

<Operations of the User Terminal Adapter 15>

The operations of the user terminal adapter 15 are described.

Figure 6:
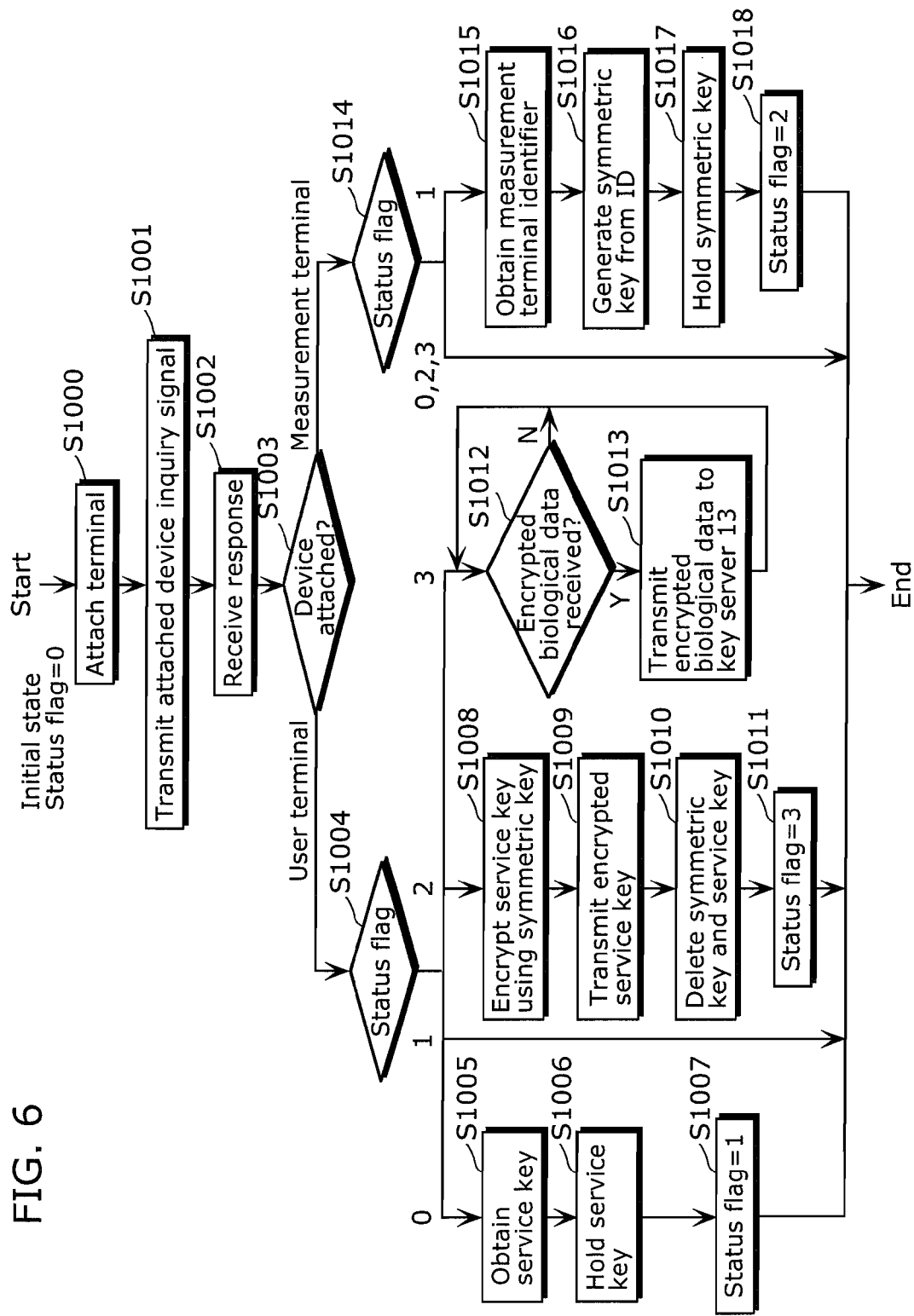
FIG. 6 is a flowchart showing the outline of the operation of the user terminal adapter according to the embodiment of the present invention.

FIG. 6 is a flowchart showing the outline of the operation of the user terminal adapter according to the embodiment of the present invention.

Here, the user terminal adapter 15 is not attached to the user terminal 14 or the measurement terminal 16 in its initial state (Status flag=0). Furthermore, the user terminal adapter 15 has a status flag and the operation is determined according to the value of the status flag.

First, the user terminal adapter 15 is attached to the user terminal 14 or the measurement terminal 16 (S1000).

The user terminal adapter 15 transmits an attached device inquiry signal to check whether the user terminal adapter 15 is attached to the user terminal 14 or the measurement terminal 16 (S1001).

The user terminal adapter 15 receives a response to the attached device inquiry signal from the user terminal 14 or the measurement terminal 16 (S1002).

The user terminal adapter 15 checks the received response and sees if the user terminal adapter 15 is attached to the user terminal 14 or the measurement terminal 16 (S1003).

Then, the user terminal adapter 15 checks the value of the status flag.

When the user terminal adapter 15 confirms that the user terminal adapter 15 is attached to the user terminal 14 and the value of the status flag is 0 (0 in S1004), the user terminal adapter 15 judges that the service key is not shared between the user terminal adapter 15 and the measurement terminal adapter 17 yet. When a message requesting registration of user information is received from the user of the user terminal 14, the user terminal adapter 15 obtains (downloads) the service key from the server 13 (S1005), and holds the obtained service key in the temporary information holding unit 1503 (S1006).

Then, the user terminal adapter 15 updates the value of the status flag to 1 (S1007), and terminates the operation.

Here, the user detaches the user terminal adapter 15 from the user terminal 14 and attaches the user terminal adapter 15 to the measurement terminal 16 (S1000). The user terminal adapter 15 performs the steps S1001 to S1003 as described above.

When the user terminal adapter 15 confirms that the user terminal adapter 15 is attached to the measurement terminal 16 and the value of the status flag is 1 (1 in S1014), receives the unique information of the measurement terminal 16 such as the measurement terminal identifier from the measurement terminal 16 (S1015).

Note that, when the user does not detach the user terminal adapter 15 from the user terminal 14 or the user mistakenly attaches the user terminal adapter 15 to the user terminal 14, the user terminal adapter 15 confirms that the user terminal adapter 15 is attached to the user terminal 14 and that the value of the status flag is 1, and then terminates the operation. Similarly, when the user terminal adapter 15 confirms that the user terminal adapter 15 is attached to the measurement terminal 16 and the value of the status flag is 0, 2, or 3, the user terminal adapter 15 terminates the operation.

Next, the user terminal adapter 15 performs a predetermined calculation based on the measurement terminal identifier obtained in the symmetric key generating unit 1506, and generates a symmetric key (S1016).

The user terminal adapter 15 stores the symmetric key generated in the symmetric key generating unit 1506 in the temporary information holding unit 1503 (S1017).

Then, the user terminal adapter 15 updates the value of the status flag to 2 (S1018), and terminates the operation.

Here, the user detaches the user terminal adapter 15 from the user terminal 16 and attaches the user terminal adapter 15 to the measurement terminal 14 again (S1000). The user terminal adapter 15 performs the steps S1001 to S1004 as described above.

When the user terminal adapter 15 confirms that the user terminal adapter 15 is attached to the user terminal 14 and it is confirmed that the value of the status flag is 2, obtains the service key and the symmetric key stored in the temporary information holding unit 1503 after it is confirmed that the user terminal adapter 15 can communicate with the measurement terminal adapter 17 attached to the measurement terminal 16. The user terminal adapter 15 encrypts, in the encryption unit 1507, the service key using the symmetric key (S1008).

The user terminal adapter 15 then transmits the encrypted service key encrypted in the encryption unit 1507 to the measurement terminal adapter 17 attached to the measurement terminal 16 (S1009).

After the encrypted service key is transmitted, the user terminal adapter 15 deletes the symmetric key stored in the temporary information holding unit 1503 (S1010). As described above, the service key stored in the temporary information holding unit 1503 is also deleted here.

Then, the user terminal adapter 15 updates the value of the status flag to 3 (S1011), and terminates the operation.

When the user terminal adapter 15 confirms that the user terminal adapter 15 is attached to the user terminal 14 and that the value of the status flag is 3, the user terminal adapter 15 receives a measured data collection request message showing that the measured data, that is, the user's biological data measured in the measurement terminal 16 is collected. After the user terminal adapter 15 checks that the user terminal adapter 15 can communicate with the measurement terminal adapter 17 attached to the measurement terminal 16, transmits the measured data collection request message to the measurement terminal adapter 17 via the internal network 12.

The user terminal adapter 15 checks if the encrypted measurement data encrypted using the service key is received in the second transmission/reception unit 1505 (S1012).

When it is confirmed that the encrypted measurement data is received (Yes in S1012), the user terminal adapter 15 stores the received encrypted measurement data in the encrypted measurement data holding unit 1502. Note that when the encrypted measurement data is not received in the second transmission/reception unit 1505 (No in S1012); the user terminal adapter 15 repeats S1012 until it is confirmed that the encrypted measurement data is received in the second transmission/reception unit 1505.

After the message, from the user terminal 14, indicating that the collected measurement data is registered at the server is received, the user terminal adapter 15 transmits, by the first transmission/reception unit 1504, the encrypted measurement data to the server 13 via the external network 11 (S1013).

As described above, the user terminal adapter 15 can generate the symmetric key securely from the measurement terminal identifier which is the unique information of the measurement terminal 16 through hand-carry by the user. Since the symmetric key is generated securely, the service key can be securely shared between the user terminal adapter 15 and the measurement terminal adapter 17. This enables secure exchange of the biological measurement data between the measurement terminal and the server. In other words, it is possible to achieve a secure communication that prevents the biological measurement data from being stolen by the malicious third party or the leak of the biological measurement data to the third party.

The specific operations of the user terminal adapter 15 are described for the following cases: (1) user registration; (2) measured data collection; (3) measured data registration; and (4) display of measured data.

(1) User Registration

When a message requesting registration of the user information from the user information registration unit 144 in the user terminal 14 is received, the first transmission/reception unit 1504 transmits the received message to the server 13 via the external network 11.

The first transmission/reception unit 1504 then receives, from the server 13 and via the external network 11, the user information registration result data including the user identifier, the user information, and the service key. When the user information registration result data is received, the first transmission/reception unit 1504 obtains the user identifier, the user information, and the service key from the user information registration result data. The first transmission/reception unit 1504 stores the obtained user identifier and the user information to the encrypted measurement data holding unit 1502, and stores the obtained service key in the temporary information holding unit 1503.

The first transmission/reception unit 1504 outputs a signal including the user identifier and the user information and indicating that the user information registration of the user identifier and the user information is completed at the server 13 to the user information registration unit 144 in the user terminal 14.

As described in the example above, the user is registered at the server 13 operated by the vender that offers health care service and provides the body weight management service.

(2) Measured Data Collection

The second transmission/reception unit 1505 receives, from the measured data collection unit 145 in the user terminal 14 via the adapter access unit 143, a measured data collection request message requesting collection of the measured data, that is, the user's biological data measured in the measurement terminal 16.

The second transmission/reception unit 1505 checks the terminal access unit 1501 to see if the user terminal adapter 15 is attached to the user terminal 14, and whether the user terminal adapter 15 can communicate with the measurement terminal adapter 17 attached to the measurement terminal 16.

When the user terminal adapter 15 is attached to the user terminal 14 and the user terminal adapter 15 can communicate with the measurement terminal adapter 17 attached to the measurement terminal 16, the second transmission/reception unit 1505 transmits the message requesting the measured data collection to the measurement terminal adapter 17 via the internal network 12.

The second transmission/reception unit 1505 then receives the encrypted measurement data which is the measured data collected by the measurement terminal adapter 17 encrypted with the service key, from the measurement terminal adapter 17 attached to the measurement terminal 16. The second transmission/reception unit 1505 then stores the received encrypted measurement data in the encrypted measured data holding unit 1502.

The second transmission/reception unit 1505 outputs a measured data collection completion message, to the user terminal adapter 15, indicating that the measured data collected by the measurement terminal adapter 17 is received by the user terminal adapter 15, and terminates the operation.

As described above, the measured data that is the body weight measured by the user is collected.

(3) Measured Data Registration

The first transmission/reception unit 1504 receives, from the measured data registration unit 146 in the user terminal 14 via the adapter access unit 143, a measured data registration request message requesting registration of the collected measured data including the user identifier.

The first transmission/reception unit 1504 then checks the terminal access unit 1501 whether the user terminal adapter 15 can communicate with the server 13.

When it is confirmed that the user terminal adapter 15 can communicate with the server 13, the first transmission/reception unit 1504 obtains the user identifier from the received measured data registration request message, and obtains the encrypted measurement data which is the user's biological measurement data encrypted with the service key, from the encrypted measurement data holding unit 1502. The first transmission/reception unit 1504 transmits the measured data including the encrypted measurement data and the user identifier to the server 13 via the external network 11.

The first transmission/reception unit 1504 receives the message (or data) indicating the completion of registration of biological measurement data in the server 13. The first transmission/reception unit 1504 transmits a message (or data) indicating the completion of registration of the biological measurement data at the server 13, to the user terminal 14 via the adapter access unit 143.

As described above, the measured data that is the body weight data measured by the user is registered at the server 13.

(4) Display of Measured Data

First, the first transmission/reception unit 1504 receives, from the measured data display processing unit 147 in the user terminal 14 via the adapter access unit 143, a measured data transmission request message. Here, the user identifier is included in the measured data transmission request message.

The first transmission/reception unit 1504 then transmits the received measured data transmission request message to the server 13 via the external network 11.

The first transmission/reception unit 1504 receives the measured data transmission data including the user identifier and the biological measurement data from the server 13 via the external network 11. The first transmission/reception unit 1504 stores the received measured data transmission data in the encrypted measurement data holding unit 1502.

The encryption unit 1507 obtains the user identifier from the received measured data transmission request message. The encryption unit 1507 then obtains the encrypted measurement data stored in the encrypted measurement data holding unit 1502 and decrypts the encrypted measurement data using the service key.

The encryption unit 1507 then transmits the decrypted measured data to the measured data display processing unit 147 via the terminal access unit 1501 and terminates the operation. Here, the service key may be stored in the temporary information holding unit 1503, or may be obtained from the server 13 again.

As described in the example above, display of the measured data is achieved by decrypting the user's measurement data obtained from the server 13 that offers the body weight management service and sending the decrypted data to the user terminal 14.

Next, the measurement terminal 16 is described.

<Configuration of the Measurement Terminal 16>

Figure 7:
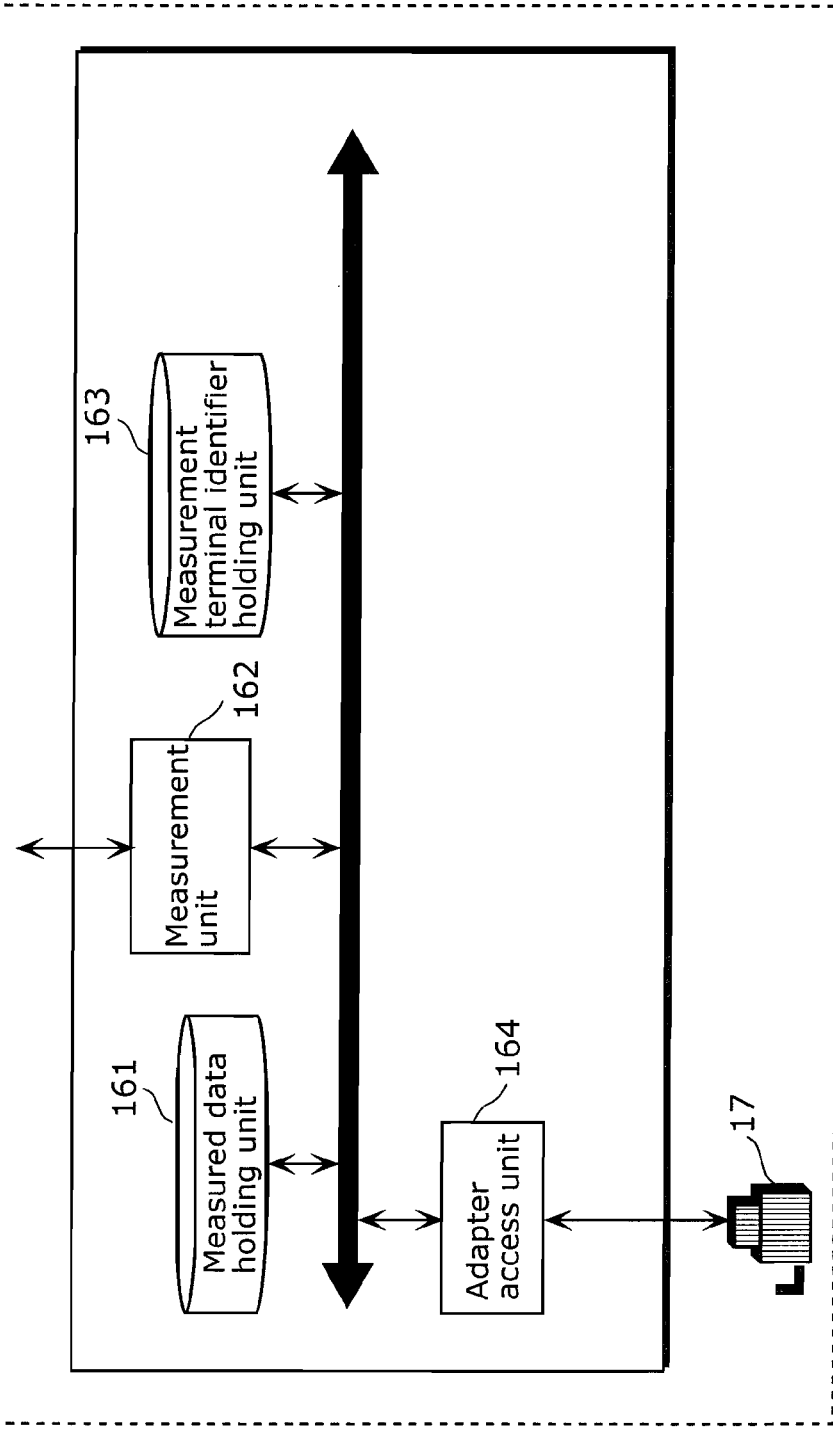
FIG. 7 shows the configuration of the measurement terminal according to the embodiment of the present invention.

FIG. 7 shows the configuration of the measurement terminal according to the embodiment of the present invention.

The measurement terminal 16 includes, as shown in FIG. 7, the measured data holding unit 161, the measurement unit 162, the measurement terminal identifier holding unit 163, and the adapter access unit 164.

The measured data holding unit 161 stores the data measured in the measurement unit 162. The measured data is composed of a set of data including the date and time of measurement and the data measured in the measurement terminal 16. For example, when the measured data is body weight data, the measured data is denoted as "2007/9/1: 70.1, 2007/9/2: 70.3 . . . 2007/9/20: 69.9."

The measurement unit 162 includes a sensor and obtains the user's biological data such as the user's body weight through measurement. Note that the measured biological data is included in the measured data and is stored in the measured data holding unit 161.

The measurement terminal identifier holding unit 163 includes, for example, a measurement terminal identifier for identifying the measurement terminal 16 as the unique information of the measurement terminal 16. The measurement terminal identifier is an identifier that has already been held upon shipment of the measurement terminal 16. The measurement terminal identifier may be a different value for each measurement terminal 16 when there are more than one measurement terminals 16, or may differ according to the models of the measurement terminals 16. Alternatively, the measurement terminal identifier may differ for each manufacturer, or for each measurable biological measurement data (body weight, blood pressure, blood glucose level, or body fat rate).

Descriptions of the adapter access unit 164 are omitted since the configuration of the adapter access unit 164 is identical to the adapter access unit 143 in the user terminal 14.

<Operations of the Measurement Terminal 16>

Next, operations of the measurement terminal 16 are described. Here, (1) data measurement is described as a specific example.

(1) Data Measurement

The measurement unit 162 includes, for example, a body weight sensor and a timer. When weighing the user's body weight, the measurement terminal 16 generates the measured data that is a combination of the date of the measurement and the body weight data, stores the generated measured data in the measured data holding unit 161, and terminates the operation.

The configuration and operations of the measurement terminal adapter 17 are described next.

Figure 8:
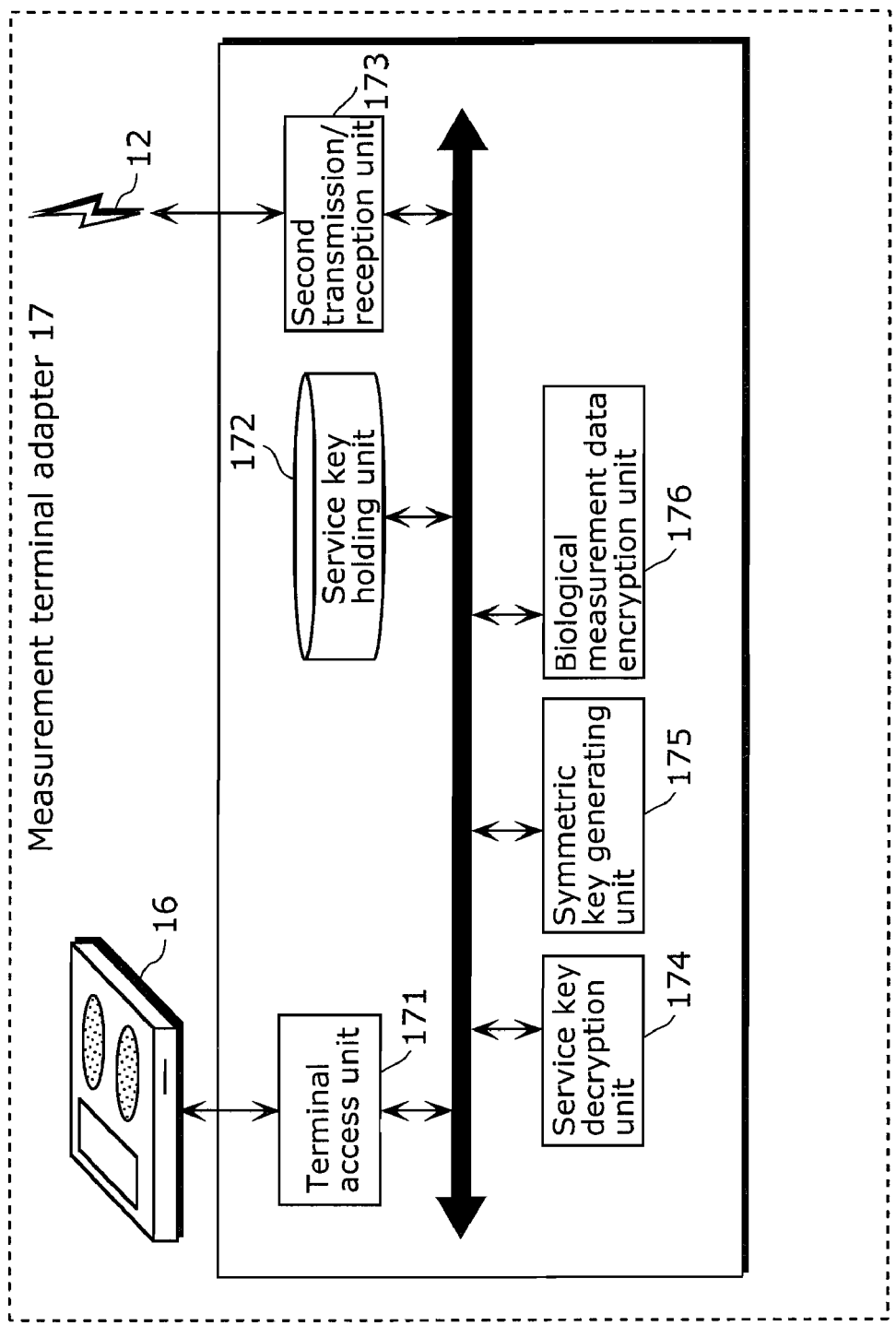
FIG. 8 shows the configuration of the measurement terminal adapter according to the embodiment of the present invention.

FIG. 8 shows the configuration of the user terminal adapter according to the embodiment of the present invention.

<Configuration of the Measurement Terminal Adapter 17>

As shown in FIG. 8, the measurement terminal adapter 17 includes the terminal access unit 171, the service key holding unit 172, the second transmission/reception unit 173, the service key decryption unit 174, the symmetric key generating unit 175, and the biological measured data encryption unit 176.

The description for the terminal access unit 171 is omitted since the configuration is identical to the terminal access unit 1501 in the user terminal adapter 15.

The service key holding unit 172 holds the service key.

The second transmission/reception unit 173 exchanges data with the second transmission/reception unit 1505 in the user terminal adapter 15 via the internal network 12. Here, the internal network 12 that transmits/receives data is implemented by, for example, Bluetooth™.

The service key decryption unit 174 checks, via the terminal access unit 171, whether the measurement terminal adapter 17 can communicate with the user terminal adapter 15 attached to the user terminal 14. When the service key decryption unit 174 can communicate with the user terminal adapter 15, the service key decryption unit 174 receives the encrypted service key from the user terminal adapter 15. The service key decryption unit 174 then obtains the symmetric key stored in the service key holding unit 172.

The service key decryption unit 174 decrypts the received encrypted service key using the obtained symmetric key. The service key decryption unit 174 stores the service key, that is, the decrypted encrypted service key in the service key holding unit 172.

Note that the service key decryption unit 174 deletes the service key stored in the service key holding unit 172 after the service key is stored in the service key holding unit 172. This is suitable for minimizing a possibility that an encryption key for encrypting biological data exchanged between the measurement terminal and the server is stolen by a malicious third party, or the leak of the biological data. Note that the service key decryption unit 174 may not delete the service key stored in the service key holding unit 172 after the service key is stored in the service key holding unit 172.

The symmetric key generating unit 175 generates a symmetric key from the unique information of the measurement terminal 16 such as the measurement terminal identifier.

The symmetric key generating unit 175 obtains the measurement terminal identifier from the measurement terminal 16 via the terminal access unit 171. The symmetric key generating unit 175 then generates a symmetric key by performing computations based on the obtained measurement terminal identifier, and stores the generated symmetric key in the service key holding unit 172.

Note that the computation method in the symmetric key generating unit 175 for generating the symmetric key is same as the computation method used by the user terminal adapter 15 for generating a symmetric key from the unique information of the measurement terminal 16 (here, a measurement terminal identifier). The computation method includes, for example, the AES cryptographic algorithm or a one-way hash function algorithm such as MD5.

The biological measurement data encryption unit 176 waits, until a measured data collection request message indicating that the measured data, that is, the user's biological data measured in the measurement terminal 16 is collected, is received from the second transmission/reception unit 1505 in the user terminal adapter 15.

When the measured data collection request message is received, the biological measurement data encryption unit 176 obtains the service key from the service key holding unit 172. The biological measurement data encryption unit 176 accesses the measured data holding unit 161 in the measurement terminal 16 and obtains the measured data. The biological measurement data encryption unit 176 then encrypts the measured data using the service key to generate the encrypted measurement data. Here, cryptographic algorithm such as the AES algorithm is used for encrypting the measured data. The biological measurement data encryption unit 176 transmits the encrypted measurement data to the second transmission/reception unit 1505 in the user terminal adapter 15.

<Operations of Measurement Terminal Adapter 17>

Next, operations of the measurement terminal adapter 17 are described.

Figure 9:
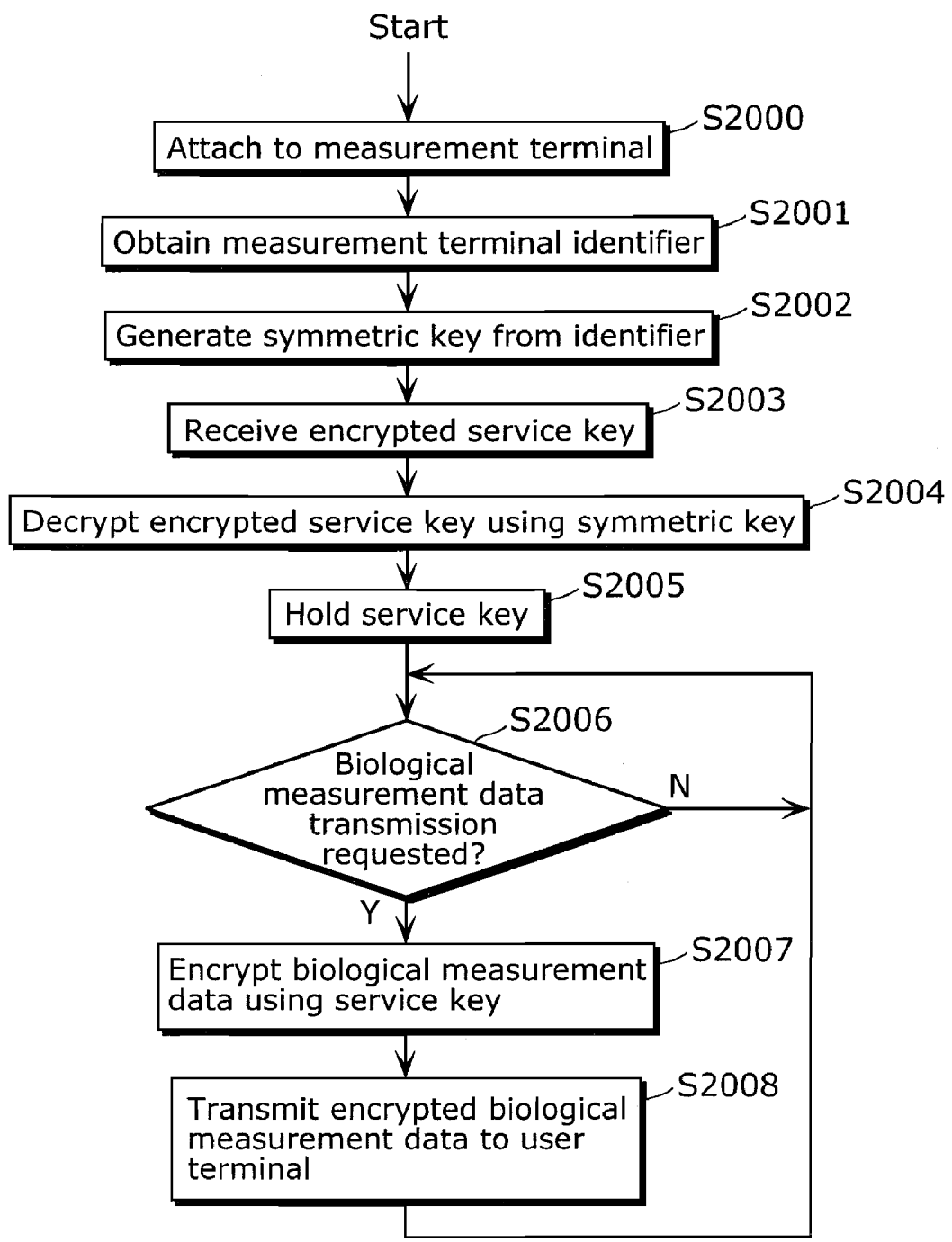
FIG. 9 is a flowchart showing the outline of the operations of the measurement terminal adapter according to the embodiment of the present invention.

FIG. 9 is a flowchart showing the outline of the operations of the measurement terminal adapter according to the embodiment of the present invention.

First, the measurement terminal adapter 17 is not attached to the measurement terminal. The user terminal adapter 17 is then attached to the user terminal 14 or the measurement terminal 16 (S2000).

The measurement terminal adapter 17 then checks if the measurement terminal adapter 17 is attached to the measurement terminal 16. When it is confirmed that the measurement terminal adapter 17 is attached to the measurement terminal 16, the measurement terminal adapter 17 obtains the unique information of the measurement terminal 16 such as the measurement terminal identifier from the measurement terminal 16 (S2001).

The measurement terminal adapter 17 generates a symmetric key from the measurement terminal identifier in the symmetric key generating unit 175 (S2002), and stores the generated symmetric key in the service key holding unit 172.

The measurement terminal adapter 17 receives the encrypted service key from the user terminal adapter 15 (S2003).

The measurement terminal adapter 17 obtains the symmetric key stored in the service key holding unit 172, and decrypts, in the service key-decryption unit 174, the received encrypted service key using the obtained symmetric key (S2004).

Next, the measurement terminal adapter 17 stores the service key decrypted in the service key decryption unit 174 in the service key holding unit 172 (S2005). Here, the measurement terminal adapter 17 deletes the symmetric key from the service key holding unit 172 after the obtained service key is stored in the service key holding unit 172.

The measurement terminal adapter 17 receives, from the user terminal adapter 15, the measured data collection request message indicating that the measured data, that is, the user's biological data measured in the measurement terminal 16 is collected (Yes in S2006). In this case, the measurement terminal adapter 17 encrypts the biological measurement data obtained from the measurement terminal 16 using the service key stored in the service key holding unit 172 (S2007).

After that, the measurement terminal adapter 17 transmits the biological measurement data encrypted using the service key to the user terminal adapter 15 (S2008).

As described above, the service key can be securely shared in the user terminal adapter 15 and the measurement terminal adapter 17 using the symmetric key generated that is obtained through hand-carry by the user, that is, the symmetric key is generated from the measurement terminal identifier. This enables secure exchange of the biological measurement data between the measurement terminal and the server. In other words, it is possible to achieve a secure communication that prevents the data from being stolen by the malicious third party or the leak to the third party.

The specific operations of the measurement terminal adapter 17 are described for the following cases: (1) user registration; and (2) measured data collection.

(1) User Registration

First, the measurement terminal adapter 17 detects that the measurement terminal adapter 17 is attached to the measurement terminal 16 via the terminal access unit 171.

The service key decryption unit 174 checks, via the terminal access unit 171, whether the measurement terminal adapter 17 can communicate with the user terminal adapter 15 attached to the user terminal 14. When the measurement terminal adapter 17 cannot communicate with the user terminal adapter 15, the service key decryption unit 174 periodically checks whether the measurement terminal adapter 17 can communicate with the user terminal adapter 15.

The service key decryption unit 174 receives the encrypted service key from the user terminal adapter 15.

Here, the symmetric key generating unit 175 obtains the measurement terminal identifier from the measurement terminal 16 via the terminal access unit 171, and performs computations based on the obtained measurement terminal identifier to generate a symmetric key. The symmetric key generating unit 175 stores the generated symmetric key in the service key holding unit 172.

The service key decryption unit 174 then obtains the symmetric key stored in the service key holding unit 172.

The service key decryption unit 174 decrypts the received encrypted service key using the obtained symmetric key.

The service key decryption unit 174 stores the service key which is the decrypted encrypted service key in the service key holding unit 172 and terminates the operation.

As described above, the measurement terminal adapter 17 securely obtains the service key when registering the user.

(2) Measured Data Collection

The biological measurement data encryption unit 176 receives a measured data collection request message indicating that the measured data, that is, the user's biological data measured in the measurement terminal 16 is collected, from the second transmission/reception unit 1505 in the user terminal adapter 15.

When the message requesting collection of measured data is received, the biological measurement data encryption unit 176 obtains the service key from the service key holding unit 172.

The biological measurement data encryption unit 176 accesses the measured data holding unit 161 in the measurement terminal 16 and obtains the biological measurement data.

The biological measurement data encryption unit 176 then encrypts the biological measurement data using the service key to generate the encrypted measurement data.

The biological measurement data encryption unit 176 transmits the encrypted measurement data to the second transmission/reception unit 1505 in the user terminal adapter 15 and terminates the operation.

As described above, the measurement terminal adapter 17 transmits the encrypted measurement data encrypted using the service key when collecting the measured data by the user.

Next, the service key distribution method of the telemedical system according to the embodiment of the present invention is described. More specifically, the description for the operation of the user terminal adapter 15 and the measurement terminal adapter 17 for securely sharing the service key is made with reference the drawings.

Figure 10:
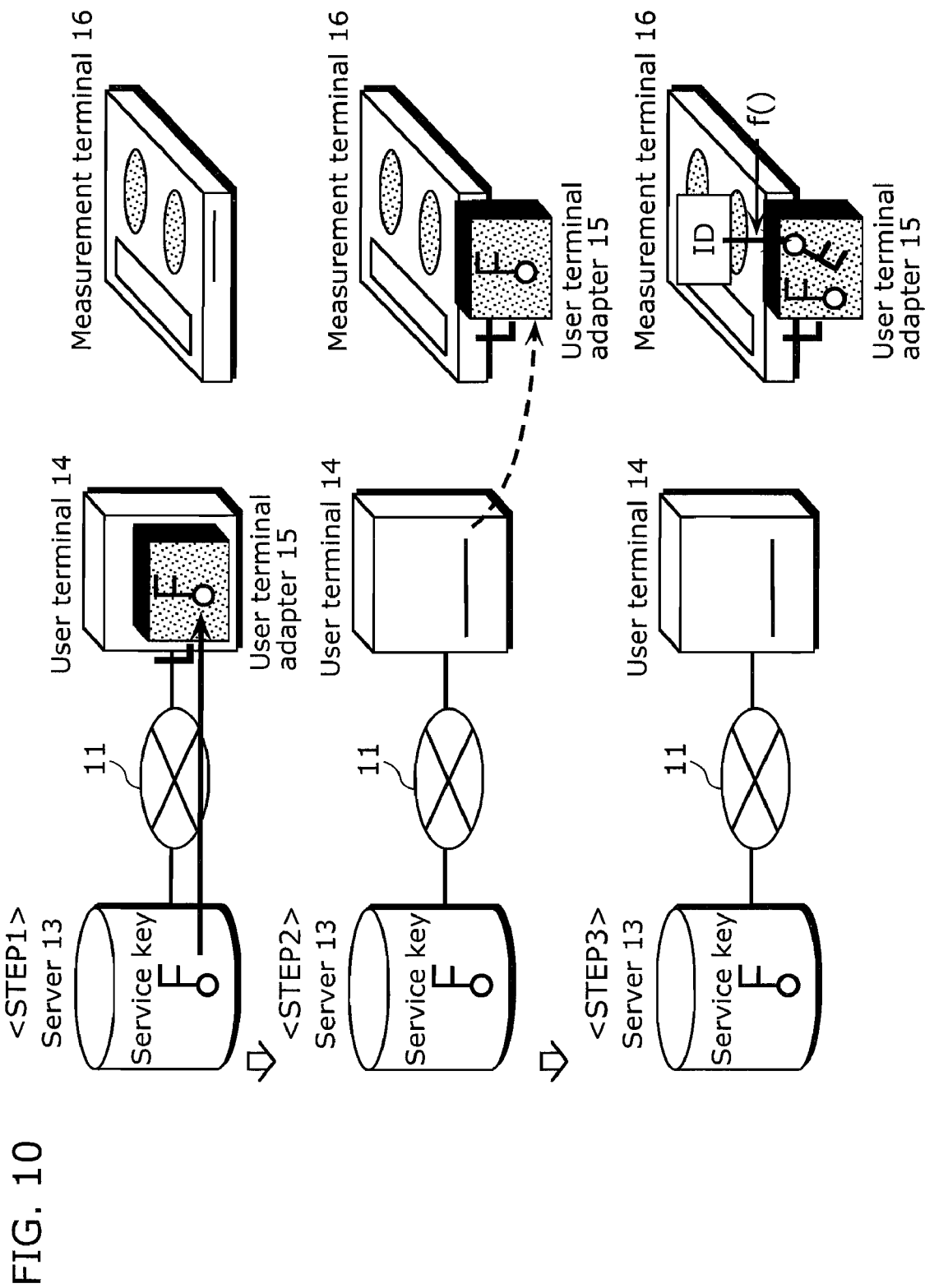
FIG. 10 shows the service key distribution method of the telemedical system according to the embodiment of the present invention.
Figure 11:
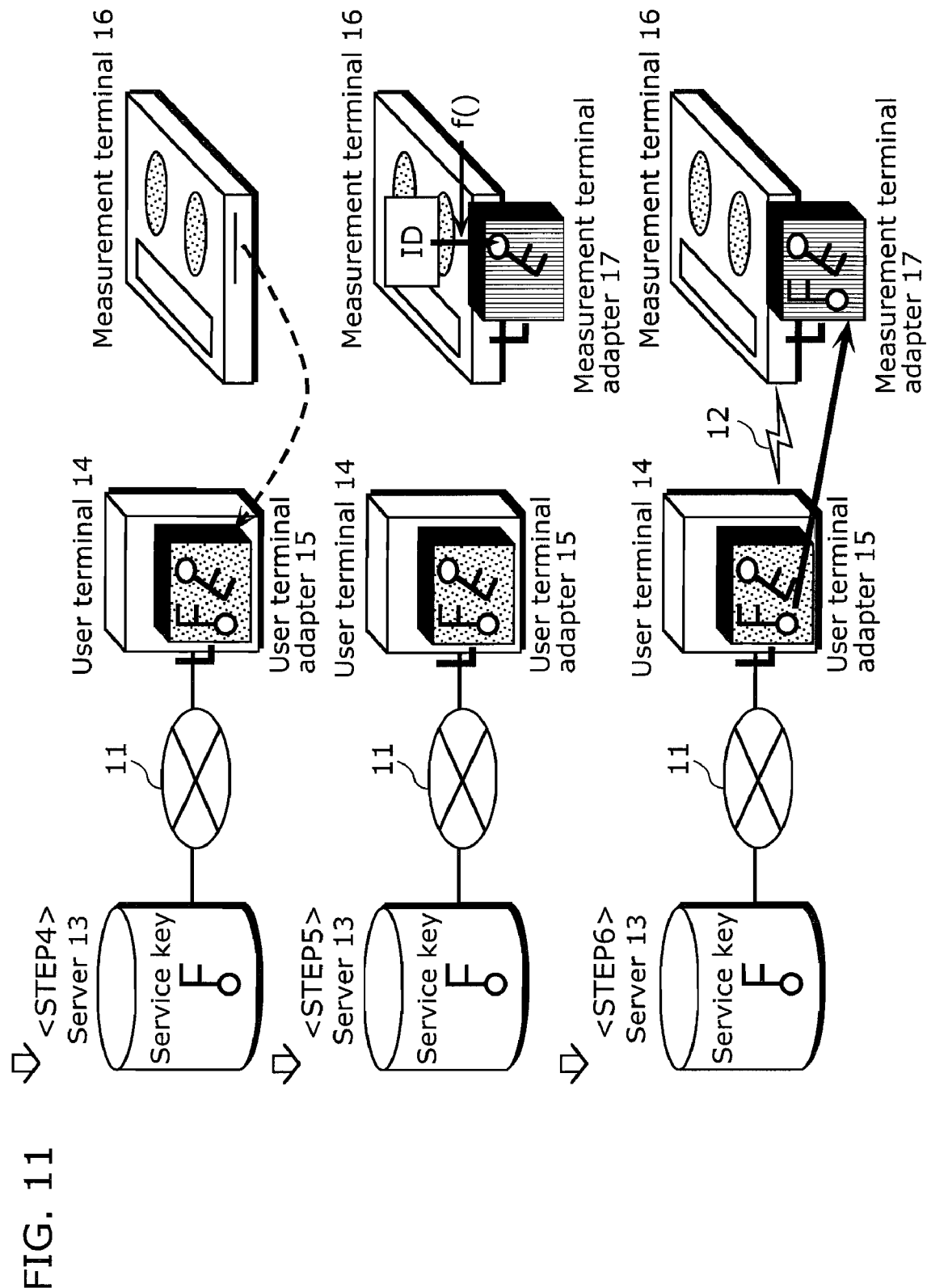
FIG. 11 shows the service key distribution method of the telemedical system according to the embodiment of the present invention.
Figure 12:
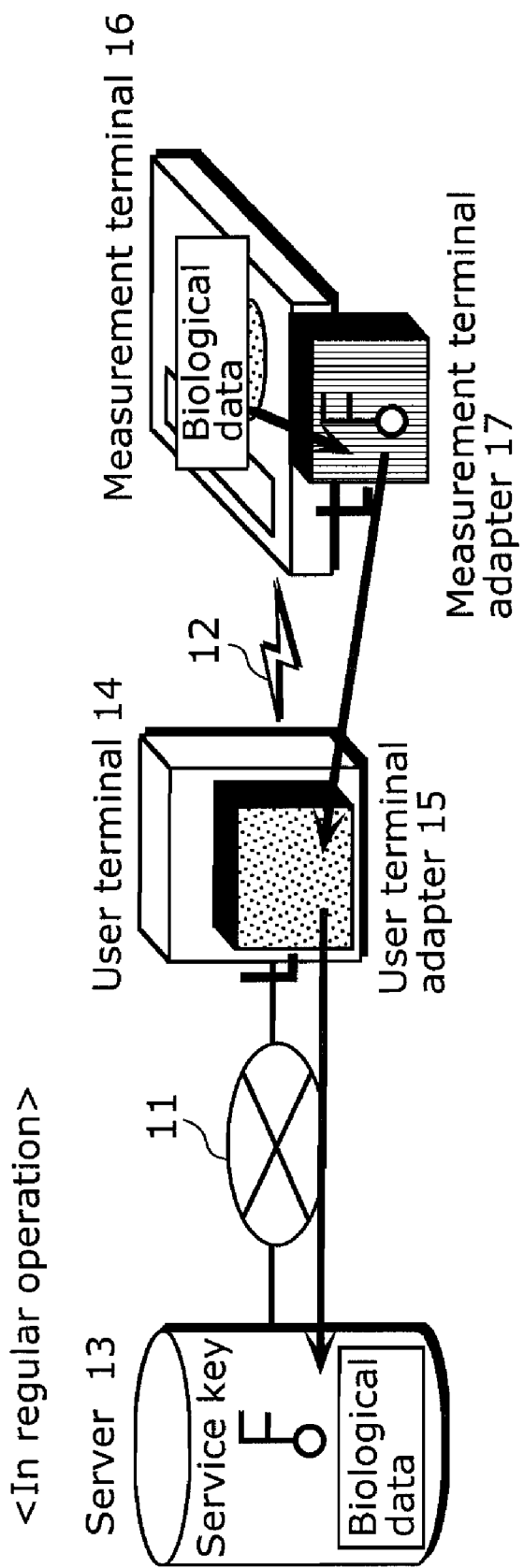
FIG. 12 is shows the regular operation of the telemedical system according to the embodiment of the present invention.
Figure 13:
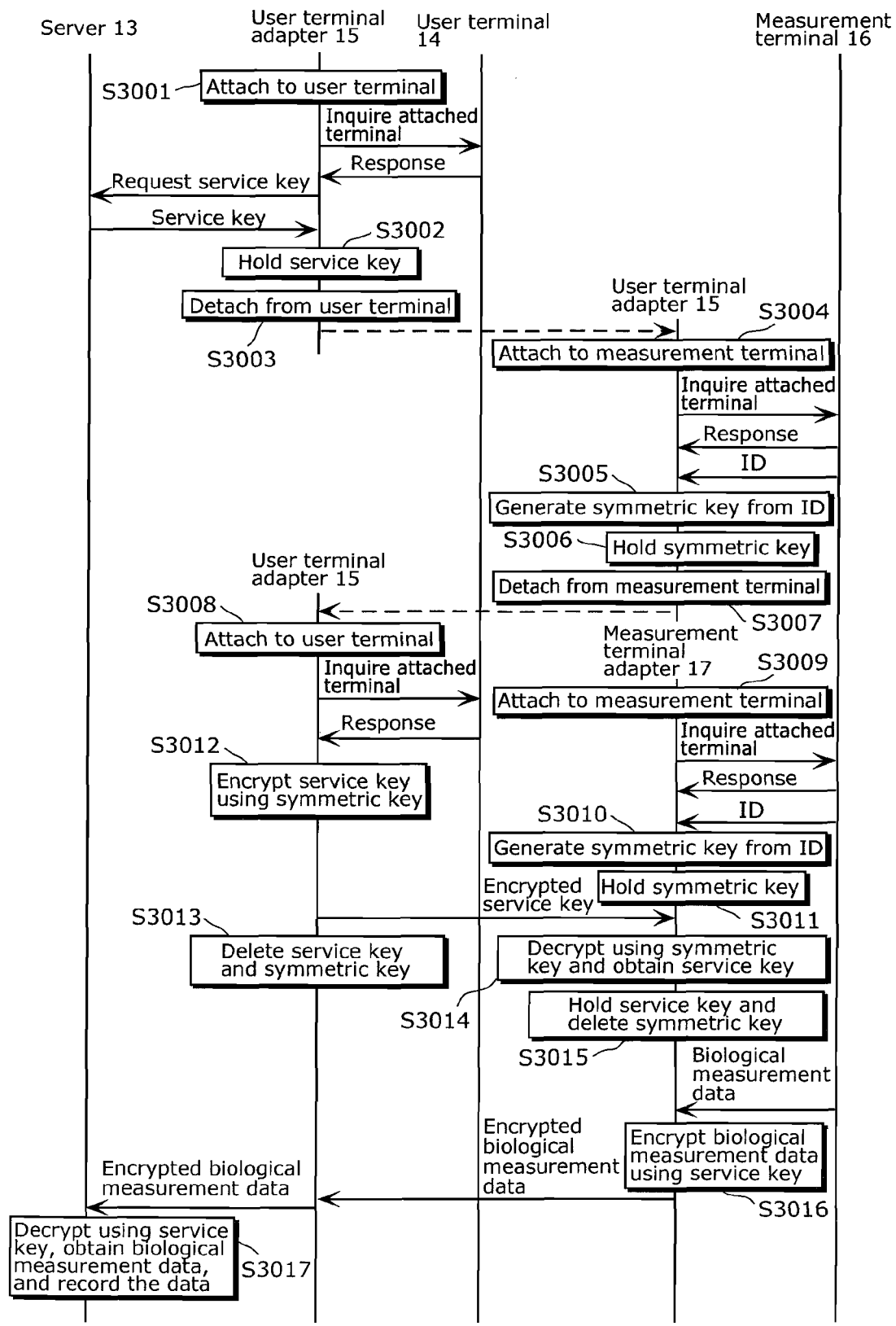
FIG. 13 is a sequence diagram for describing the operations in the telemedical system according to the embodiment of the present invention.

FIGS. 10 and 11 are diagrams for describing the service key distribution method of the telemedical system according to the embodiment of the present invention. FIG. 12 is a diagram for describing the regular operation of the telemedical system according to the embodiment of the present invention. FIG. 13 is a sequence diagram for describing the operations in the telemedical system according to the embodiment of the present invention. Hereafter, the description is basically made with reference to FIG. 13.

First, the user terminal adapter 15 is attached to the user terminal 14 by the user (S3001). The user terminal adapter 15 transmits an attached device inquiry signal to check whether the user terminal adapter 15 is attached to the user terminal 14 or the measurement terminal 16, and receives the response.

After that, as shown in STEP 1 in FIG. 10, when the user terminal adapter 15 confirms that the user terminal adapter 15 is attached to the user terminal 14, the user terminal adapter 15 requests the service key to the server 13, and obtains the service key from the server 13. The user terminal adapter 15 holds the obtained service key (S3002).

Note that the steps S3001 to S3002 correspond to S1000 to S1007 in FIG. 6.

After that, as shown in STEP 2 in FIG. 10, the user detaches the user terminal adapter 15 from the user terminal 14 (S3003), and attaches the user terminal adapter 15 to the measurement terminal 16 (S3004). The user terminal adapter 15 transmits an attached device inquiry to check whether the user terminal adapter 15 is attached to the user terminal 14 or the measurement terminal 16, and receives the response.

After that, as shown in STEP 3 in FIG. 10, when the user terminal adapter 15 confirms that the user terminal adapter 15 is attached to the measurement terminal 16, the user terminal adapter 15 obtains the measurement terminal identifier from the measurement terminal 16. The user terminal adapter 15 generates a symmetric key from the measurement terminal identifier (S3005), and holds the generated symmetric key (S3006).

Note that the steps S3004 to S3006 correspond to S1000 to S1004 and S1015 to S1018 in FIG. 6.

After that, as shown in STEP 4 in FIG. 11, the user detaches the user terminal adapter 15 from the measurement terminal 16 (S3007) and attaches the user terminal adapter 15 to the user terminal 14 (S3008). The user terminal adapter 15 transmits an attached device inquiry to check whether the user terminal adapter 15 is attached to the user terminal 14 or the measurement terminal 16, and receives the response.

Here, as shown in STEP 5 in FIG. 11, the measurement terminal adapter 17 is attached to the measurement terminal 16 (S3009). The measurement terminal adapter 17 transmits an attached device inquiry to check whether the measurement terminal adapter 17 is attached to the user terminal 14 or the measurement terminal 16, and receives the response. After that, when the measurement terminal adapter 17 confirms that the measurement terminal adapter 17 is attached to the measurement terminal 16, the measurement terminal adapter 17 obtains the measurement terminal identifier from the measurement terminal 16. The measurement terminal adapter 17 generates a symmetric key from the measurement terminal identifier (S3010), and holds the generated symmetric key (S3011).

The steps S3009 to S3011 correspond to S2000 to S2002 in FIG. 9.

After that, as shown in STEP 6 in FIG. 11, the user terminal adapter 15 encrypts the service key being held using the symmetric key being held (S3012). The user terminal adapter 15 transmits the service key encrypted by the symmetric key to the measurement terminal adapter 17, and deletes the symmetric key and the service key being held after the transmission (S3013). The measurement terminal adapter 17 receives the encrypted service key from the user terminal adapter 15. The measurement terminal adapter 17 decrypts the received encrypted service key using the symmetric key being held, and obtains the service key (S3014). When the obtained service key is held (S3015), the measurement terminal adapter 17 deletes the symmetric key being held.

Note that the steps S3012 to S3013 correspond to S1008 to S1010 in FIG. 6. The steps S3014 to S3015 correspond to S2004 to S2005 in FIG. 9.

After that, as shown in FIG. 8, the measurement terminal adapter 17 obtains the biological measurement data from the measurement terminal 16, and encrypts the obtained biological measurement data using the service key (S3016). The measurement terminal adapter 17 transmits the biological measurement data encrypted using the service key to the user terminal adapter 15. When the encrypted biological measurement data from the measurement terminal adapter 17 is received, the user terminal adapter 15 transmits the received encrypted biological measurement data to the server 13. When the encrypted biological measurement data is received, the server 13 decrypts the encrypted biological measurement data using the service key being held, obtains the biological measurement data, and records the obtained biological measurement data (S3017).

As described above, the service key is distributed in the telemedical system 1, and biological measurement data is exchanged between the measurement terminal and the server.

As described above, in the telemedical system 1 according to the embodiment, the symmetric key is generated from the unique information of the measurement terminal 16 obtained by the user terminal adapter 15 through hand-carry by the user without a possibility of the leak of data to the malicious third party, and is transmitted to the measurement terminal adapter 17 after the service key is encrypted using the symmetric key generated by the user terminal adapter 15. With this, the measurement terminal adapter 17 can securely obtain the service key which is an encryption key, and thus the exchange of biological measurement data can be securely performed between the measurement terminal and the server. In other words, it is possible to achieve a secure communication that prevents the data from being stolen by the malicious third party or the leak of the data to the third party.

In addition, in the telemedical system 1 according to the present embodiment, the service key is held in the adapters, namely, the user terminal adapter 15 and the measurement terminal adapter 17, not in the user terminal 14 and the measurement terminal 16 in order to prevent the leak to the malicious third party.

Furthermore, the possibility of leak of the data to the malicious third party is eliminated by deleting, from the user terminal adapter 15 and the measurement terminal adapter 17, the symmetric key used for obtaining the service key after the measurement terminal adapter 17 obtained the service key, and by further deleting the service key held by the user terminal adapter 15.

Note that, the embodiment describes an example in which the encryption unit 1507 in the user terminal adapter 15 performs decryption of the encrypted measurement data stored in the user terminal adapter 15 when the measured data is displayed in the user terminal 14 and encryption of the service key received from the server 13 when the user terminal 14 transmits the service key to the measurement terminal adapter 17. This is preferable to suppress the increase in cost of the terminal device and to improve versatility of the terminal device since communication function and cryptographic functions are not incorporated in the terminal device side of the user terminal 14 and the measurement terminal 16.

However, the embodiment is not limited to the example, and the user terminal 14 may perform, among the computations performed by the user terminal adapter 15, only cryptographic computations. Similarly, the measurement terminal 16 may perform, among the computations performed by the measurement terminal adapter 17, only the cryptographic computation of the measurement terminal adapter 17. With this, reduction of the computation amount on the user terminal adapter 15 and the measurement terminal adapter 17 can be achieved.

In addition, the communication function, the cryptographic function, or a part of the cryptographic function of the user terminal adapter 15 or the measurement terminal adapter 17 may be incorporated in the user terminal 14 or the measurement terminal 16.

Furthermore, in the embodiment, the configuration where the user terminal 14 stores the encrypted measurement data in the user terminal adapter 15 without holding the measured data is described. However, the present invention is not limited to the embodiment. The encrypted measurement data may be stored in the user terminal 14.

The embodiment described above is an example of implementation of the present invention. The present invention is not limited to the embodiment, and may be implemented without departing from the scope of the invention. For example, the present invention includes the following cases.

(1) There may be multiple servers 13, user terminals 14, and user terminal adapters 15.

(2) The measurement performed in the measurement terminal 16 may not be limited to body weight data. Body temperature, blood pressure, body fat rate, or blood glucose level may be measured.

(3) Different service keys may be given to each user.

(4) Secure communication path may be established between the server 13 and the user terminal 14, using Secure Socket Layer (SSL), for example.

(5) Communication function may be incorporated into the user terminal 14 or the measurement terminal 16 in advance.

(6) The process divided between the user terminal 14 and the user terminal adapter 15 may be divided differently from the embodiment. In addition, the process divided between the measurement terminal 16 and the measurement terminal adapter 17 may be divided differently from the embodiment.

(7) Although Bluetooth™ was listed as an example of the internal network 12, the internal network 12 may be implemented with other communication method such as IEEE 802.11a/b/g/n or Zig bee.

(8) Although AES was listed as an example of the cryptographic algorithm, other cryptographic algorithms such as 3DES may also be used.

(9) Although MD5 was listed as an example of the hash function algorithm which computes a symmetric key from the measurement terminal identifier in the symmetric key generating unit 1506 in the user terminal adapter 15 and in the symmetric key generating unit 175 in the measurement terminal adapter 17, other hash function algorithm such as Secure Hash Algorithm 1 (SHA-1) may also be used.

Each of the above-described devices is a computer system including a microprocessor, a ROM, a RAM, a hard disc unit, a display unit, a keyboard, and a mouse. A computer program is recorded on the RAM or the hard disc unit. Functions of each device are achieved through the operation of the microprocessor according to the computer program. The computer program is configured of a combination of command codes indicating instructions to the computer for achieving the predetermined functions.

Furthermore, a part of, or all of the components of each of the devices may be configured of a system Large Scale Integration (LSI). The system LSI is an ultra multi-function LSI having multiple components integrated into one chip, and more specifically, is a computer system that includes a microprocessor, a ROM, and a RAM and others. A computer program is recorded on the RAM. Functions of the system LSI are achieved through the operation of the microprocessor according to the computer program.

Furthermore, a part of, or all of the components of each of the devices may be configured of an IC card or a single module that is detachable/attachable to each device. The IC card or the module is a computer system configured of a microprocessor, a ROM, and a RAM and others. The IC card and the module may include the ultra multi-function LSI. Functions of the IC card or the module are achieved through the operation of the microprocessor according to the computer program. The IC card or the module may be tampering-resistant.

The present invention may be implemented as the method described above. Furthermore, the present invention may be implemented as a computer program for implementing the method on a computer, and the computer program may also be expressed as digital signals.

Furthermore, the present invention may be implemented as a computer-readable recording medium on which the computer program and the digital signals are recorded, such as a flexible disc, a hard disc, a CD-ROM, an MO, a DVD, a DVD-ROM, a DVD-RAM, a Blu-ray Disc (BD), and a semiconductor memory. Alternatively, the present invention may be implemented as the digital signals recorded on the recording media.

In the present invention, the computer program or the digital signals may be transmitted via a telecommunication line, wireless or wired line, a network such as the Internet, or a data broadcast.

The present invention is a computer system including a microprocessor and a memory, and the memory stores the computer program, and the microprocessor may operate according to the computer program.

Furthermore, the program or the digital signals may be implemented in another independent computer system through recording the program and the digital signals on the recording medium and transferring the program and digital signals.

Although only an exemplary embodiment of the telemedical system according to this invention has been described in detail above, those skilled in the art will readily appreciate that many modifications are possible in the exemplary embodiment without materially departing from the novel teachings and advantages of this invention. Accordingly, all such modifications are intended to be included within the scope of this invention.

Industrial Applicability

The present invention may be used for a telemedical system, and may also be used for various services including logistics, transportation, education using sensors and IC tags.

What is claimed is:

1. A telemedical system comprising:
a first adapter that is attachable to a measurement terminal that obtains biological data of a user of the measurement terminal by measuring the user and to a management apparatus that manages the measured biological data;
a second adapter that is attachable to the measurement terminal; and
a server which communicates with said first adapter,
wherein said first adapter includes:
a key holding unit configured to receive, from the server, a service key used for encrypting the biological data and to store the received service key, when said first adapter is attached to the measurement terminal;
a first symmetric key generating unit configured to obtain unique information of the measurement terminal from the measurement terminal and to generate a symmetric key based on the obtained unique information, when said first adapter is attached to the measurement terminal after said first adapter is detached from the management apparatus while the service key is stored in said key holding unit;
a key encryption unit configured to encrypt the service key using the symmetric key and to store the encrypted service key in said key holding unit, when said first adapter is attached to the management apparatus after said first adapter is detached from the measurement terminal; and a first communication unit configured to transmit the encrypted service key to said second adapter, when said first adapter is attached to the management apparatus and when said second adapter attached to the measurement terminal, and wherein said second adapter includes:

a second symmetric key generating unit configured to obtain from the measurement terminal the unique information of the measurement terminal and to generate a symmetric key based on the obtained unique information, when said second adapter is attached to the measurement terminal;

a key decryption unit configured to decrypt the encrypted service key using the symmetric key generated in said second symmetric key generating unit, when said second adapter receives the encrypted service key from said first adapter; and a second communication unit configured to encrypt, using the decrypted service key, the biological data of the user measured by the measurement terminal and to transmit the encrypted biological data to said server via said first adapter.

2. The telemedical system according to claim 1, wherein, in said first adapter, said first symmetric key generating unit does not generate the symmetric key when said first adapter is attached to the measurement terminal while the service key is not stored in said key holding unit.

3. The telemedical system according to claim 2, wherein said first symmetric key generating unit is configured to delete the symmetric key and the service key after said first communication unit transmits the encrypted service key to said second adapter.

4. The telemedical system according to claim 3, wherein said second symmetric key generating unit is configured to delete the symmetric key generated in said second symmetric key generating unit after said key decryption unit decrypts the encrypted service key using the symmetric key.

5. The telemedical system according to claim 4, wherein said first symmetric key generating unit generates the symmetric key based on the unique information of the measurement terminal using a predetermined calculation method, and wherein said second symmetric key generating unit generates the symmetric key based on the unique information of the measurement terminal using the predetermined calculation method.

6. The telemedical system according to claim 5, wherein said first symmetric key generating unit and said second symmetric key generating unit respectively generate the symmetric key using an cryptographic algorithm using a cryptographic key as the predetermined calculation method.

7. The telemedical system according to claim 5, wherein said first symmetric key generating unit and said second symmetric key generating unit generates the symmetric key using a hash function as the predetermined calculation method.

8. The telemedical system according to claim 7, wherein said first symmetric key generating unit and said second symmetric key generating unit generates the symmetric key using a unique identifier of the measurement terminal as the unique information of the measurement terminal.

9. The telemedical system according to claim 8, wherein each of said first adapter and said second adapter is one of a memory card and a USB device.

10. A first adapter in a telemedical system including the first adapter, a second adapter, and a server, said first adapter being attachable to a measurement terminal that measures biological data of a user of the measurement terminal and being attachable to a management apparatus that manages the measured biological data, wherein said second adapter is attachable to the measurement terminal, and said server communicating with said first adapter, said first adapter comprising:

a key holding unit configured to receive, from the service key used for encrypting the biological data and to store the received service key, when said first adapter is attached to the measurement terminal;

a symmetric key generating unit configured to obtain unique information of the measurement terminal from the measurement terminal and to generate a symmetric key based on the obtained unique information, when said first adapter is attached to the measurement terminal after said first adapter is detached from the management apparatus while the service key is stored in said key holding unit;

a key encryption unit configured to encrypt the service key using the symmetric key and to store the encrypted service key in said key holding unit, when said first adapter is attached to the management apparatus after said first adapter is detached from the measurement terminal; and a communication unit configured to transmit the encrypted service key to said second adapter, when said first adapter is attached to management apparatus and when the second adapter is attached to the measurement terminal.

11. A second adapter in a telemedical system including a first adapter, said second adapter, and a server, said first adapter being attachable to a measurement terminal that measures biological data of a user of the measurement terminal and being attachable to a management apparatus that manages the measured biological data, wherein said second adapter is attachable to the measurement terminal, and wherein said server communicating with the first adapter, said second adapter comprising:

a symmetric key generating unit configured to obtain from the measurement terminal the unique information of the measurement terminal and to generate a symmetric key based on the obtained unique information, when said second adapter is attached to the measurement terminal;

a key decryption unit configured to decrypt the encrypted service key using the symmetric key generated in said second symmetric key generating unit, when said second adapter receives the encrypted service key from said first adapter, the encrypted service key being transmitted from the first adapter when the first adapter is attached to the management apparatus after the first adapter is detached form the measurement terminal; and a communication unit configured to encrypt, using the decrypted service key, the biological data of the user measured by the measurement terminal and to transmit the encrypted biological data to said server via said first adapter.

12. A service key transmission method for a telemedical system, the telemedical system including:
- a first adapter that is attachable to a measurement terminal that obtains biological data of a user of the measurement terminal by measuring the user and to a management apparatus that manages the measured biological data;
- a second adapter that is attachable to the measurement terminal; and
- a server which communicates with said first adapter, said service key transmission method comprising:
- receiving, at the first adapter from the server, a service key used for encrypting the biological data and stores the received service key in the first adapter, when the first adapter is attached to the measurement terminal;
- obtaining, at the first adapter from the measurement terminal, unique information of the measurement terminal and generating, at the first adapter, a symmetric key based on the obtained unique information, when the first adapter is attached to the measurement terminal after the first adapter is detached from the management apparatus while the service key is stored in the first adapter;
- encrypting, at the first adapter, the service key using the symmetric key and storing the encrypted service key in the first adapter, when the first adapter is attached to the management apparatus after the first adapter is detached from the measurement terminal;
- transmitting, from the first adapter to the second adapter, the encrypted service key, the second adapter is attached to the management apparatus and when the second adapter is attached to the measurement terminal;
- obtaining, at the second adapter from the first adapter, the unique information and generating a symmetric key based on the obtained unique information, when the second adapter is attached to the measurement terminal;
- decrypting, at the second adapter, the encrypted service key using the generated symmetric key, when the second adapter receives the encrypted service key from the first adapter; and
- encrypting, at the second adapter using the decrypted service key, the biological data of the user measured by the measurement terminal and transmitting the encrypted biological data from the second adapter to the server via the first adapter.

13. A non-transitory computer-readable recording medium having stored thereon a service key transmission program for a telemedical system, the telemedical system including:
- a first adapter that is attachable to a measurement terminal that measures biological data of a user of the measurement terminal and to a management apparatus that manages the measured biological data;
- a second adapter that is attachable to the measurement terminal; and
- a server which communicates with said first adapter, wherein, when executed, said service key transmission program causes the telemedical system to execute a method comprising:
- a key holding step in which the first adapter receives, from the server, a service key used for encrypting the biological data and stores the received service key in the first adapter, when the first adapter is attached to the measurement terminal;
- a first symmetric key generating step in which the first adapter obtains unique information of the measurement terminal from the measurement terminal and generates a symmetric key based on the obtained unique information, when the first adapter is attached to the measurement terminal after the first adapter is detached from the management apparatus while the service key is stored in the first adapter;
- a key encryption step in which the first adapter encrypts the service key using the symmetric key and stores the encrypted service key in the first adapter, when the first adapter is attached to the management apparatus after the first adapter is detached from the measurement terminal;
- a first communication step in which the first adapter transmits the encrypted service key to the second adapter, when the first adapter is attached to the management apparatus and when the second adapter is attached to the measurement terminal,
- a second symmetric key generating step in which the second adapter obtains, from the measurement terminal, the unique information of the measurement terminal and generates a symmetric key based on the obtained unique information, when the second adapter is attached to the measurement terminal;
- a key decryption step in which the second adapter decrypts the encrypted service key using the symmetric key generated in said second symmetric key generating step, when the second adapter receives the encrypted service key from the first adapter; and
- a second communication step in which the second adapter encrypts, using the service key decrypted in said key decryption step, the biological data of the user measured by the measurement terminal and transmits the encrypted biological data to the server via the first adapter.

* * * * *